(12) United States Patent
Wilson et al.

(10) Patent No.: US 8,067,230 B2
(45) Date of Patent: Nov. 29, 2011

(54) PROSTATIC STEM CELLS, ISOLATION AND USES

(75) Inventors: Elaine Lynette Wilson, New York, NY (US); Patricia Burger, Bloubergstrand (ZA)

(73) Assignee: New York University, New York, NY (US)

( * ) Notice: Subject to any disclaimer, the term of this patent is extended or adjusted under 35 U.S.C. 154(b) by 482 days.

(21) Appl. No.: 11/596,351

(22) PCT Filed: May 10, 2005

(86) PCT No.: PCT/US2005/016284
§ 371 (c)(1),
(2), (4) Date: Oct. 29, 2007

(87) PCT Pub. No.: WO2005/113753
PCT Pub. Date: Dec. 1, 2005

(65) Prior Publication Data
US 2008/0194710 A1      Aug. 14, 2008

Related U.S. Application Data

(60) Provisional application No. 60/570,811, filed on May 14, 2004.

(51) Int. Cl.
*C12N 5/00* (2006.01)
*C12N 5/02* (2006.01)

(52) U.S. Cl. ....................................................... 435/325
(58) Field of Classification Search ................... 435/325
See application file for complete search history.

(56) References Cited

U.S. PATENT DOCUMENTS 6,004,528 A * 12/1999 Bergstein ..................... 424/1.49
6,984,522 B2 * 1/2006 Clarke et al. .................. 435/374

OTHER PUBLICATIONS

Collins et al. J. of Cell Sci, 114: 3865-3872, 2001.*
Goto et al. Abstract #394, Journal of Urology, (Apr. 2004) vol. 171, No. 4, Supplement, pp. 104. print. Meeting Info.: Annual Meeting of the American Urological Association. San Francisco, CA, USA. May 8-13, 2004.*

* cited by examiner

*Primary Examiner* — Thaian N Ton
(74) *Attorney, Agent, or Firm* — Browdy and Neimark, PLLC

(57) ABSTRACT

Prostatic stem cells have been isolated. Benign prostatic hyperplasia and other proliferative diseases of the prostate may arise in prostatic stem cells. The prostatic stem cells are used as a research tool for studying cancer and other proliferative diseases of the prostate, and for developing diagnostics and therapeutics for proliferative diseases of the prostate. Antibodies to the antigens expressed by prostatic stem cells can be used as therapeutics or diagnostics or can be used to deliver therapeutic or diagnostic agents directly to the prostatic stem cells.

4 Claims, 18 Drawing Sheets

PROSTATIC STEM CELLS, ISOLATION AND USES

CROSS-REFERENCE TO RELATED APPLICATIONS

The present application claims priority from provisional application No. 60/570,811, filed May 14, 2004, the entire contents of which are hereby incorporated by reference.

GOVERNMENT LICENSE RIGHTS

The U.S. Government has a paid-up license in this invention and the right in limited circumstances to require the patent owner to license others on reasonable terms as provided for by the terms of Contract No. DK52634 awarded by the National Institutes of Health of the Department of Health and Human Services, and Contract No. PCO30614 awarded by the U.S. Army. In addition, some of the work described in the present application was supported by the University of Cape Town Staff Research Fund and the SA Medical Research Council.

FIELD OF THE INVENTION

The present invention relates to isolating prostatic stem cells and their use with respect to the diagnosis, staging and treatment of prostatic diseases.

BACKGROUND OF THE INVENTION

Stem cells are rare cells located in specific niches where they are maintained in a quiescent state (Spradling et al, 2001; Lavker et al, 2000). Stem cells have been defined as cells that have the ability to perpetuate themselves through self-renewal and to generate mature cells of a particular tissue through differentiation. Although one would assume that each tissue arises from a tissue-specific stem cell, rigorous identification and isolation of these somatic stem cells has been accomplished only in a few instances.

Stem cells in organs other than the prostate have been identified by their expression of specific antigens, such as stem cell antigen-1 (Sca-1), alpha 6 integrin, and Bcl-2. The present inventors have determined that these antigens can be used to identify the stem cell population in the proximal region of ducts. Sca-1 is expressed on the surface of stem/progenitor cells from a variety of murine tissues, such as hematopoietic (Spangrude et al, 1988), cardiac (Matsuura et al, 2004), mammary gland (Welm et al, 2002), skin (Montanaro et al, 2003), muscle (Asakura, 2003) and testis (Falciatori et al, 2004). Alpha 6 integrin (CD49f) is expressed on the surface of primitive cells in the liver (Suzuki et al, 2000) and skin (Tani et al, 2000). Anti-alpha 6 integrin antibodies have been used to enrich for spermatogonial stem cells from mouse testis (Shinohara et al, 1999). Bcl-2, an intracellular anti-apoptotic protein (Adams et al, 1998), may protect primitive cells from death and is expressed by hematopoietic, keratinocyte and colon stem cells (Domen et al, 2000a; Potten et al, 1997; Tiberio et al, 2002). The expression of CD133 (prominin) has been found on human putative prostatic stem cells (Richardson et al, 2004). Signaling molecules such as Wnt and Notch are also involved in stem cell renewal and stem cell niches (Walsh et al, 2003). Notch1 expression has been noted in prostate epithelial cells during normal development and in prostate cancer cells (Shou et al, 2001).

The most definitive evidence for stem cells' definition is their ability to reconstitute an organ. Serially transplanted bone marrow can reconstitute lethally irradiated mice (Chen et al, 2000; Maggio-Price et al, 1988), and the number of successful serial transfers depends on the size of the grafts and the time intervals between transfers (Jones et al, 1989).

Cell surface molecules on various types of cells are given a cluster of differentiation (CD) designation in which each CD molecule designation describes a surface molecule (marker) identifiable by a cluster of monoclonal antibodies that display the same cellular reactivity. CD designations are assigned at regularly held international workshops on human leukocyte differentiation antigens. For example, the CD19 marker is specific to B cells, and the CD33 marker is specific to myeloid cells. At the present time, it is not known how many of the markers associated with differentiated cells are also present on stem cells.

Cancer is caused primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Pre-malignant abnormal cell growth is exemplified by hyperplasia, metaplasia, or most particularly, dysplasia. The neoplastic lesion may evolve clonally and develop an increasing capacity for growth, metastasis, and heterogeneity, especially under conditions in which the neoplastic cells escape the host's immune surveillance.

As understanding of the pathophysiological role of cancer increases, the role of both tumor markers and genetic information becomes more important in the management and treatment of cancer patients. Tumor markers are substances that can be measured quantitatively by biochemical or immunochemical means in tissue or body fluids to detect a cancer, to establish the extent of tumor burden before treatment, to diagnose as aides in staging or confirmation of histopathology, to predict the outcome of drug therapy, and to monitor relapse. Measurement of tumor markers has been used to screen total populations as well as for testing high-risk groups.

Stem cell biology and tumorigenesis may be closely linked, and stem cells may have a role in the etiology of cancer (Al-Hajj et al, 2004; Al-Hajj et al, 2003; Lapidot et al, 1994; Pardal et al, 2003; Reya et al, 2001; WO 03/050502). Stem cells and tumor cells have many common features, including self-renewal, multi-drug resistance, telomerase expression and, in the instance of the prostate, androgen independence. It has been reported in WO 03/050502 that a small percentage of tumorigenic cells within an established solid tumor have the properties of stem cells. These solid tumor stem cells give rise both to more solid tumor stem cells and to the majority of cells in the tumor, cancer cells that have lost the capacity for extensive proliferation and the ability to give rise to new tumors. Thus, solid tumor cell heterogeneity reflects the presence of a variety of tumor cell types that arise from a solid tumor stem cell.

Prostatic stem cells do not require androgens for survival, as evidenced by completely normal prostatic regeneration after more than 30 cycles of androgen ablation and supplementation, which results in involution and normal regeneration of this gland (Isaacs, 1985). As prostatic carcinoma usually progresses to an androgen-independent tumor (which may reflect a stem cell-like phenotype), an understanding of prostate cell biology is important for devising preventative or therapeutic approaches to prostate cancer.

In addition to being a target of carcinogenesis, prostatic stem cells may also be a potential source of benign prostate hyperplasia, or BPH (De Marzo et al, 1998). The isolation of these cells would therefore be likely to increase our understanding not only of normal prostate physiology but also of two of the most common diseases afflicting men, namely prostatic carcinoma and BPH.

The murine prostate consists of a branched ductal network with each duct consisting of a proximal region (adjacent the urethra), an intermediate region, and a distal region. Actively proliferating cells (transit amplifying cells) are located in the distal region of the ducts (Cunha et al, 1987a). The present inventors have previously shown that the proximal region of mouse prostatic ducts is enriched in a subpopulation of epithelial cells that have a number of properties of stem cells: they are slow-cycling, possess high in vitro proliferative potential, and single cells are able to reconstitute complex, highly branched glandular structures in vitro that contain basal and luminal cells (Tsujimura et al, 2002). In addition, cell digests from the proximal region contain cells that form significantly more prostatic tissue in an in vivo transplantation model than cells isolated from other prostatic regions. Furthermore, cell digests obtained from this transplanted tissue are again able to give rise to prostatic tissue when re-inoculated into new animals, confirming the location of prostatic stem cells in the proximal region.

It would be useful to isolate a subpopulation of cells in the prostate that have the attributes of stem cells, particularly because a characteristic of stem cells is their ability to engraft and proliferate in their "niche" within their compartment.

As stem cells in other organs have been identified by their expression of specific antigens, it would be useful to determine whether these antigens could be used to identify the prostatic stem cell population in the proximal region of ducts.

Isolation of prostatic stem cells and the elucidation of their phenotype would make it possible to examine their biology and their regenerative capacity. In addition, the relationship between prostatic stem cells and two common diseases of the prostate, benign prostatic hyperplasia (BPH) and prostate carcinoma could be studied, as both diseases may arise from prostatic stem cells (De Marzo et al, 1999). It has recently been proposed that stem cells are the cells most likely to accumulate mutations that result in neoplasia, and that tumors may contain a stem cell reservoir that can self-renew indefinitely (Reya et al, 2001; Passegue et al, 2003).

The phenotype of acute myelogenous leukemia cells is similar to that of hematopoietic stem cells (Bonnet et al, 1997), and tumorigenic breast cancer cells also resemble normal early multipotent breast epithelial cells (Al-Hajj et al, 2003). Therefore, it would be useful to isolate prostatic stem cells in order to permit an understanding of prostatic epithelial biology, which is relevant as the evolution of androgen-independent prostate carcinoma may reflect a stem-like state of the tumor (Reya et al, 2001; Passegue et al, 2003). Moreover, stem cells and tumor cells have many common features, including infinite life span, androgen independence, multi-drug resistance, and telomerase expression. Therefore, isolation and characterization of special features of these stem calls may make it possible to design rational therapies to treat prostate carcinoma and BPH.

SUMMARY OF THE INVENTION

It is an object of the present invention to overcome the aforementioned deficiencies in the prior art.

It is another object of the invention to isolate prostatic stem cells.

It is a further object of the present invention to assay for prostatic stem cells by identifying antigens prostatic stem cells do or do not express.

It is a further object of the present invention to provide a tool for studying cancer and other proliferative diseases of the prostate.

It is still another object of the present invention to provide a method for selectively targeting therapeutic diagnostic agents to the most aggressive portions of a prostatic tumor site or site of metastasis.

It is yet another object of the present invention to provide a tool for determining the stage or degree of aggressiveness of prostate cancer and likelihood of metastasis.

It is another object of the present invention to provide a tool for monitoring the efficacy of therapeutic drugs administered to a patient with prostate cancer or other proliferative diseases of the prostate.

A subpopulation of cells in the proximal region of prostatic ducts has been identified that express both Sca-1 and alpha 6 integrin, as well as Bcl-2, fibroblast growth factor receptor (FGFR), preferably FGFR-1, prominin (CD 133), CD34, Notch protein (Notch), preferably Notch1 and receptors for the Wnt proteins (the receptors that bind the Wnt proteins are called the Frizzled proteins), preferably Fzd3. These cells, expressing markers for stem cells, have a phenotype distinct from cells present in the remaining regions of the ducts. This population of Sca-1$^{high}$ cells co-express at least one of alpha 6 integrin, Bcl-2, FGFR, prominin, CD34, Notch and Frizzled proteins, particularly Fzd3. Cells with these properties are almost absent from the remaining regions of ducts. The Sca-1 expressing cells isolated from the proximal region give rise to large amounts of prostate tissue in an in vivo transplantation assay, whereas cells that do not express this antigen form very little tissue, establishing that prostatic stem cells reside within the Sca-1 expressing population in the proximal region of ducts.

Prostatic stem cells can be purified from isolated proximal duct regions by virtue of their high expression of the Sca-1 surface antigen, particularly in combination with at least one other antigen, namely, Bcl-2, FGFR, alpha 6 integrin, prominin, CD34, Notch and Frizzled proteins. While Sca-1 is a murine antigen not found in humans, the other seven markers are found in humans and would be expected to selectively identify prostatic stem cells in humans.

Prostatic stem cells can thus be identified by the antigens they express, such as alpha 6 integrin, Sca-1, Bcl-2, FGFR, prominin, CD34, Notch and Frizzled proteins. Gene chip analysis can be used to determine which other molecules are expressed preferentially by these cells as compared with, for example, distal cells or proximal cells that do not express these antigens. This makes it possible to identify molecules that may be useful therapeutically, as well as those that may aid in isolating the prostatic stem cells.

In addition to the antigens noted above, other markers for prostatic stem cells include CXCR4, Thy-1, Hedgehog, c-kit and members of the Polycomb family, such as Bmi1 and EZH2, and other proteins known to be expressed by stem cells.

Additionally, it is possible to determine different molecules expressed by the prostatic stem cells. This is effected by using techniques that subtract the molecules expressed by, e.g., distal cells from the molecules expressed by, e.g., proximal cells, or by subtracting the molecules that are expressed by proximal cells that lack Sca-1, alpha 6 integrin, Bcl-2, prominin, CD34, Notch, FGFR and/or Frizzled proteins from those molecules that are expressed by those cells that do have such markers.

A subpopulation of cells in the proximal region of prostatic ducts has been identified that express Sca-1, alpha 6 integrin, Bcl-2, FGFR, prominin, CD34, Notch and Frizzled proteins.

Cells expressing this combination of markers have a phenotype distinct from cells present in the remaining regions of the ducts. This population expresses high levels of Sca-1 and more than 60% of the Sca-1$^{high}$ cells co-express alpha 6 integrin and Bcl-2. High levels of Sca-1 can be used to identify prostatic stem cells in the proximal region with high proliferative potential, whereas lower levels of Sca-1 identify the transit-amplifying cells in the remaining regions of ducts that have more limited growth potential. Prostatic stem cells are therefore concentrated in the proximal region of ducts and express high levels of Sca-1 together with alpha 6 integrin, Bcl-2, FGFR, prominin, CD34, Notch and Frizzled proteins. These markers can be used to define the prostatic stem cell population and can be used in diagnosis.

Efficacy of therapeutic regimens can be determined by assaying for these highly proliferating cells before, during, and after administration of the chemical or biological agents. Furthermore, the degree of aggressiveness versus dormancy of the particular tumor can be assessed by determining the presence of prostatic stem cells in a tumor biopsy. The greater the number of stem cells, the greater the aggressiveness and likelihood of metastasis. The lower the percent of prostatic stem cells, the slower the expected growth of the tumor. This staging of the aggressiveness of the tumor is an important aspect of the present invention.

BRIEF DESCRIPTION OF THE DRAWINGS

FIG. 1A is a schematic diagram of the prostate showing the protocol used to implant cells removed from different regions of prostatic ducts under the renal capsule.

FIG. 1B shows the result of combining cells from the urethra or different regions of ducts with urogenital sinus mesenchyme (UGM) cells implanted under the renal capsule. The grafts were harvested after eight weeks, weighed, and used for immunocytochemical examination.

FIG. 1C shows prostatic tissue under the renal capsule initiated with $10^5$ proximal cells.

FIG. 1D shows prostatic tissue under the renal capsule imitated with $10^5$ distal cells.

FIG. 1E shows a section of prostatic tissue arising from proximal cells showing basal cells (arrows) immunohistochemically stained using an antibody against K5 keratin.

FIG. 1F shows a section of prostatic tissue arising from proximal cells showing luminal cells (arrows) immunohistochemically stained using an antibody against K8 keratin.

FIG. 1G shows a section of prostatic tissue arising from proximal cells immunohistochemically stained with antibodies specific for prostatic secretory products (arrows).

FIG. 1H shows a section of proximal prostatic tissue stained with control antibodies showing that the staining in FIG. 1G is specific.

FIG. 3A shows the weight of tissue from the distal and proximal region.

FIG. 3B compares the weights of tissues obtained from the proximal and the distal region.

FIG. 4A is a schematic diagram showing the protocol used for examining the androgen sensitivity of prostate cells.

FIG. 4B shows the result of combining cells from the urethra or different regions of ducts with UGM cells and implanted under the renal capsule of intact animals (8w A+), castrated animals (16w A−) or animals that had been castrated for eight weeks followed by androgen supplementation for eight weeks (8w A$^-$/8w A$^+$). The grafts were harvested at the times indicated in FIG. 4A, weighed, and used for immunocytochemical examination.

FIG. 4C shows sections of prostate tissue from intact animals stained with hematoxylin and eosin.

FIG. 4D shows sections of prostate tissue from intact animals immunohistochemically stained using an antibody against alpha smooth muscle actin. The sections were counterstained with hematoxylin.

FIG. 4E shows sections of prostate tissue from castrated animals stained with hematoxylin and eosin.

FIG. 4F shows sections of prostate tissue from castrated animals immunohistochemically stained using an antibody against alpha smooth muscle actin. The sections were counterstained with hematoxylin.

FIG. 4G shows sections of prostate tissue from castrated and replenished animals stained with hematoxylin and eosin.

FIG. 4H shows sections of prostate tissue from castrated and androgen replenished animals immunohistochemically stained using an antibody against alpha smooth muscle actin. The sections were counterstained with hematoxylin.

FIGS. 5A-5E show results obtained when cells from all or selected regions of the prostate were combined with UGM cells and implanted under the renal capsule of intact animals FIG. 5A shows cells from all regions of the prostate.

FIG. 5B shows cells from the proximal region of the ducts.

FIG. 5C shows cells from the intermediate region of the ducts.

FIG. 5D shows cells from the distal region of the ducts.

FIG. 5E shows cells from the urethra.

FIGS. 5F-5J show results obtained when cells from all or selected regions of the prostate were combined with UGM cells and implanted under the renal capsule of castrated animals. After eight weeks of androgen deprivation, androgens were administered for an additional eight weeks, after which the animals were sacrificed.

FIG. 5F shows cells from all regions of the prostate.

FIG. 5G shows cells from the proximal region of ducts.

FIG. 5H shows cells from the intermediate region of ducts.

FIG. 5I shows cells from the distal region of ducts.

FIG. 5J shows cells from the urethra.

FIG. 9A shows that the proximal region contained 2.9 fold more Sca-1 expressing cells than the remaining ductal regions.

FIG. 9B shows that cells from the proximal region expressed 2.8 fold more molecules of Sca-1 per cell (higher MFI) than cells from the remaining regions of ducts.

FIG. 9C shows that cells with high levels of Sca-1 expression were nine-fold more prevalent in the proximal region of ducts than in the remaining regions.

FIG. 9D is a representative histogram of Sca-1 expression by viable cells from the proximal region (thick line) and the remaining regions (thin line) of ducts, and shows the differences in Sca-1 expression between these two regions. The gray filled histogram represents the appropriate IgG control. The marker, MI, is placed so that less than 1% of control cells are positive. A second marker denotes Sca-$1^{high}$ cells.

FIG. 10A shows that the proximal region contained significantly more (26.1 fold) Sca-$1^{high}$ alpha 6 integrin cells than the remaining ductal regions.

FIG. 10B shows representative dot plots from one of four experiments showing that Sca-$1^{high}$ alpha 6 integrin cells are present in the proximal region (22.2%).

FIG. 10C shows that Sca-$1^{high}$ alpha 6 integrin cells are almost absent (0.2%) in the remaining regions of ducts.

FIG. 11A shows that the proximal region contains 54.5 fold more Sca-$1^{high}$/Bcl-$2^+$ cells than the remaining ductal regions.

FIG. 11B shows representative dot plots from one of five experiments showing that Sca-$1^{high}$/Bcl-$2^+$ cells are present in the proximal region (8.7%).

FIG. 11C shows that Sca-$1^{high}$/Bcl-$2^+$ cells are almost absent (0.1%) in the remaining regions of the ducts.

FIG. 12A shows that the proximal region contained 19.6 fold more Sca-$1^+$/alpha 6 integrin$^+$/Bcl-$2^+$ cells than the remaining regions.

FIG. 12B is a dotplot showing that 50.3% of proximal Sca-$1^+$ cells co-expressed both alpha 6 integrin and Bcl-2.

FIG. 12C shows that 7.0% of Sca-$1^+$ cells from the remaining regions co-expressed both alpha 6 integrin and Bcl-2.

FIG. 12D shows the results of an analysis of triple labeled cells expressing high levels of Sca-1, showing that the proximal region contained 98 fold more Sca-$1^{high}$/alpha 6 integrin$^+$/Bcl-$2^+$ cells than the remaining regions.

FIG. 12E shows that more than 70% of proximal in Sca-$1^{high}$ cells expressed both alpha 6 integrin$^+$ and Bcl-2.

FIG. 12F shows that 2% of Sca-$1^{high}$ cells from the remaining regions were Sca-$1^{high}$/alpha 6 integrin$^+$/Bcl-$2^+$ cells.

FIG. 14A shows unsorted cells.

FIG. 14B shows separation of the unsorted cells into Sca-1 enriched cells.

FIG. 14C shows separation of unsorted cells into Sca-1 depleted populations.

FIG. 15A shows that Sca-$1^{high}$ cells formed 6.3 fold more prostatic tissue under the renal tissue than Sca-$1^{med/low}$ cells and 7.5 fold more prostatic tissue than Sca-$1^{negative}$ cells.

FIG. 15B shows prostate tissue under the renal capsule initiated with $3\times10^4$ Sca-$1^{high}$, Sca-$1^{med/low}$, and Sca-$1^{negative}$ cells isolated by FACS from the proximal region of the ducts.

FIG. 15C shows paraffin sections stained with hematoxylin and eosin illustrating the morphology of prostatic tissue arising from Sca-$1^{high}$, Sca-$1^{med/low}$, and Sca-$1^{negative}$ cells. The prostatic tissue obtained from Sca-$1^{high}$ cells had normal prostatic histology comprising basal and luminal cells lining prostatic ducts. The lumens of the ducts were filled with secretory material. The tissue arising from the Sca-$1^{med/low}$, and Sca-1$^{negative}$ cells contained increased stroma with less of an epithelial component, and not much secretory material was noted within the ducts.

FIG. 18A is a dotplot indicating the FCS/SSC properties of viable cells from the proximal region of prostatic ducts.

FIG. 18B is a dot blot of cells stained with Hoechst 33342 dye showing a side population comprising 0.65% of cells.

FIG. 18C shows control antibody staining of cells from the side population, indicating no non-specific staining.

FIG. 18D shows double staining with antibodies against Sca-1 and alpha 6 integrin.

FIG. 18E shows the FSC/SSC properties of the Sca-1$^+$ alpha 6 integrin$^+$ side population cells, indicating that these cells are of medium size (medium FSC) and are relative agranular (low SSC).

DETAILED DESCRIPTION OF THE INVENTION

Figure 1:
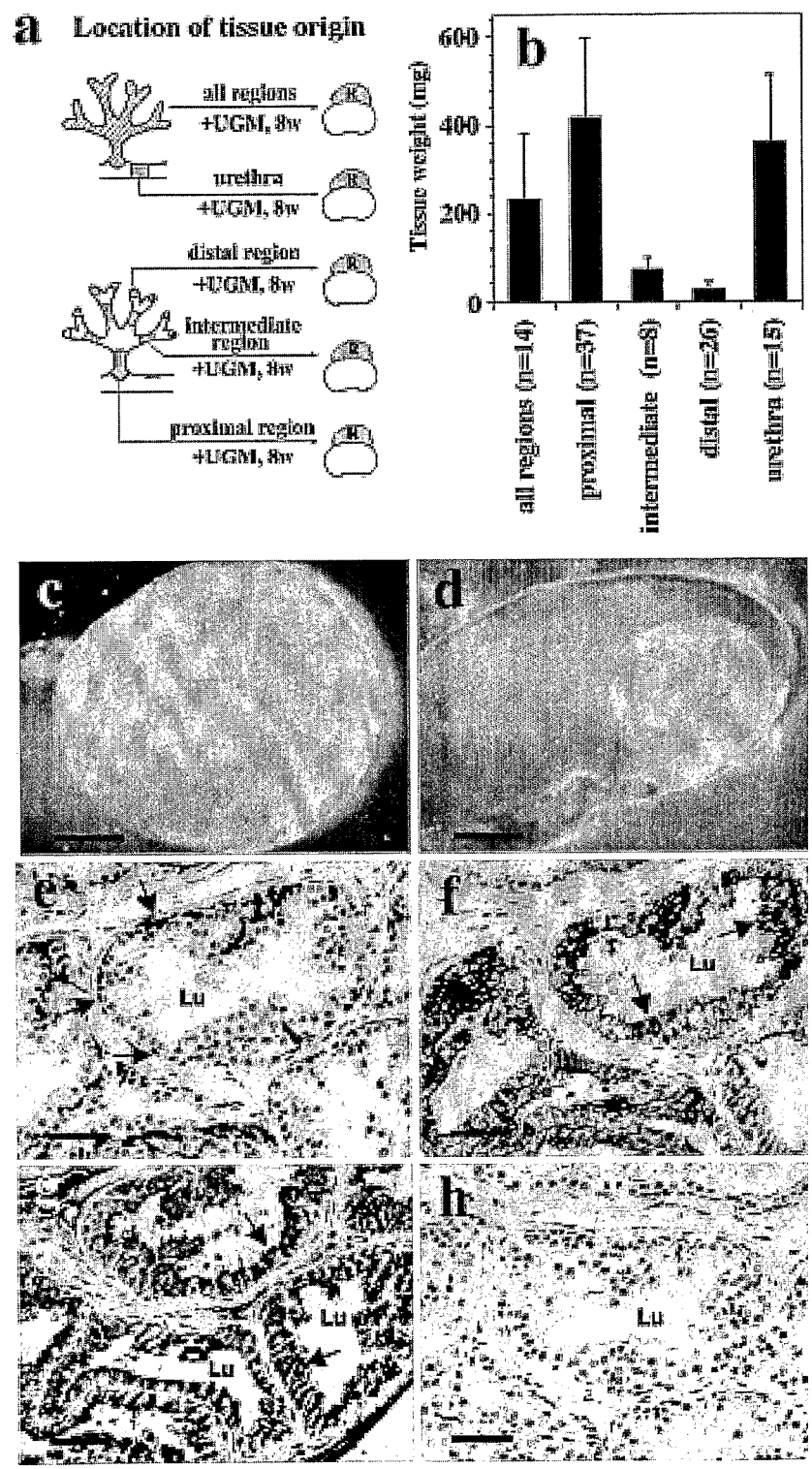
FIG. 1 shows that the proximal region of mouse prostatic ducts and the urethra contain stem cells.

Stem cells in organs other than the prostate have been identified by their expression of specific antigens, such as stem cell antigen-1 (Sca-1), alpha 6 integrin, Bcl-2, FGFR, prominin, CD34, Notch and Frizzled proteins. The present inventors have determined that these antigens can be used to identify the stem cell population in the proximal region of ducts of the prostate.

The most definitive evidence for stem cell definition is their ability to reconstitute an organ. Serially transplanted bone marrow can reconstitute lethally irradiated mice (Chen et al, 2000; Maggio-Price et al, 1988), and the number of successful serial transfers depends on the size of the grafts and the time intervals between transfers (Jones et al, 1989). In order to determine the location of prostatic stem cells, cells were isolated from different regions of prostatic ducts as well as from the urethra. These cells were combined with embryonic urogenital sinus mesenchyme (UGM). These recombinants were inserted under the renal capsule to study the proliferative potential and androgen sensitivity of the different cell populations in vivo. It was found that cells isolated from the proximal region and the urethra have significantly greater proliferative ability in vivo than those cells isolated from the distal or the intermediate regions of ducts.

Remarkably, the prostatic tissue that arose in vivo from isolated proximal cells maintained a proximal-distal axis under the renal capsule, and cells isolated form the proximal region of ducts in these sub-renal capsule grafts similarly exhibited a greater proliferative capacity than cells isolated from the distal ductal regions of grafts. Proximal ductal cells can be isolated and passaged through four successive generations of sub-renal capsule grafts, indicating that cells with high proliferative potential are located in the proximal regions of both primary prostatic tissue and sub-renal tissue grafts. Cells in the proximal region also withstand prolonged periods of androgen deprivation and regenerate prostate tissue normally once androgens are administered. Conversely, those cells isolated from distal and intermediate regions survive poorly in the absence of androgens.

It has also been discovered that prostatic stem cells can be purified from isolated proximal duct regions by virtue of their high expression of the Sca-1 surface antigen. Sca-1 expressing cells isolated from the proximal region of ducts form significantly more prostatic tissue (203.0±83.1 mg) in an in vivo prostate reconstitution assay than Sca-1 depleted cells (11.9±9.2 mg). Almost all of the proliferative capacity resides within the cells that express high levels of Sca-1, and the proximal regions of prostatic ducts contain 9.0 fold more Sca-1$^{high}$ cells than the remaining regions. More than 60% of these cells co-express alpha 6 integrin and Bcl-2, which are also expressed by stem cells of other origins. Prostatic stem cells can therefore be isolated based on Sca-1 expression. Further stratification of the phenotype of these cells makes it possible to develop rational therapies for treating prostate cancer and benign prostatic hyperplasia.

Stem cells are rare cells, and as large numbers of cells isolated from prostatic ducts express Sca-1, it is unlikely that all Sca-1 expressing cells are stem cells. Our data indicate that prostatic stem cells reside in the Sca-1$^{high}$ population that also express alpha 6 integrin, Bcl-2, FGFR and prominin, as well as Frizzled Protein, CD34 and Notch.

The prostate cells from the proximal region that express high levels of Sca-1 also co-express the antigen Bcl-2. The presence of Bcl-2 in Sca-1 expressing prostatic stem cells may protect these cells from apoptotic death. Stem cells are needed for the lifetime of their host and mechanisms to protect them from death are important to insure their long-term survival. The Bcl-2 protein suppresses apoptosis (Adams et al, 1998) and is present in many long-lived cells (Hockenbery et al, 1991).

Bcl-2 protects hematopoietic and keratinocyte stem cells from apoptotic death (Domen et al, 2000b; Tiberio et al, 2002) and over-expression of Bcl-2 increases the numbers of hematopoietic stem cells in vivo (Domen et al, 2000a) and protects hematopoietic stem cells from the harmful effects of a number of chemotherapeutic agents, thus insuring their survival (Domen et al, 2003). The expression of Bcl-2 by the prostatic stem cell population that has high levels of Sca-1 and significant in vivo proliferative potential is therefore likely to insure the long-term survival of this cell population.

High levels of Bcl-2 in the proximal stem cell region may also be required to protect the cells in this region from apoptosis and death that accompanies androgen withdrawal. Castration results in an increase in TGF-β levels (Kyprianou et al, 1989) leading to apoptosis and involution of the more distal regions of the gland, while the proximal region is relatively unchanged (Rouleau et al, 1990; Sugimura et al, 1986b). We find a TGF-β signaling gradient in prostatic ducts, with high levels of signaling in the quiescent proximal region (high Bcl-2 expression) and low levels of signaling in the distal region (low Bcl-2 expression) (data not shown). The proximal region is therefore protected from TGF-β-mediated apoptosis by high Bcl-2 expression. Aberrant regulation of Bcl-2 expression may contribute to the etiology of prostatic diseases such as BPH (Colombel et al, 1998), proliferative inflammatory atrophy, which is a regenerative lesion that may give rise to prostate cancer (De Marzo et al, 1999), and to prostate cancer itself (McDonnell et al, 1992). In addition, the over-expression of Bcl-2 is implicated in the formation of hormone-independent prostate tumors, as it inhibits the apoptotic effect of TGF-β and androgens (Bruckheimer et al, 2003). The identification of the phenotype of prostatic stem cells that express high levels of Bcl-2 may therefore aid in identifying the target cells in which these lesions originate.

Activation of the Notch receptor has previously been implicated in breast cancer and Notch signaling plays a role in transformation of cells transfected with an activated Ras oncogene (Berry et al, 1997; Morrison et al, 2000). CD34 has also been previously shown to be a stem cell marker in hematopoietic cells (Burger et al, 2002).

Tables I-III show the expression of Sca-1, alpha 6 integrin, Bcl-2, FGFR and prominin by cells from the proximal region of prostatic ducts compared with cells from the remaining ductal regions. Thus, expression of these antigens can be used to identify stem cells for detecting disease, monitoring therapy and tumor aggressiveness or targeting for therapy.

As cancers may arise from mutations in stem cells (Al-Hajj et al, 2004; Pardal et al, 2003; Reya et al, 2001) and as BPH may result from aberrant proliferation of these cells (De Marzo et al, 1998), the identification of the stem cell phenotype of prostate cells permits the development of rational targeted therapies for treating both BPH and prostate cancer.

The unique isolated cells of the present invention are separated from other cells by virtue of their markers.

Samples were enriched for alpha 6 integrin and Sca-1 expressing cells by immunomagnetic separation using antibodies to these antigens and magnetically activated cell sorter (MACS) microbeads, magnetic columns and the MiniMACS system (Miltenyi Biotec, Auburn, Calif.).

"Enriched", as in an enriched population of cells, is defined based upon the increased number of cells having a particular marker in a fractionated set of cells as compared with the number of cells having the marker in the unfractionated set of cells. The enriched population is preferably enriched in the specified markers at least two fold relative to the unfractionated cell population, more preferably, it is enriched at least four fold, and most preferably at least ten fold.

Table III shows that expression of Sca-1, prominin and FGFR by cells from the proximal region of the prostatic ducts were much greater compared with cells from the remaining ductal regions from intact and castrated mice.

The cells can be isolated by any conventional techniques for separating cells, such as those described in Civin, U.S. Pat. Nos. 4,714,680; 4,965,204; 5,035,994; and 5,130,144; Tsukamoto et al, 5,750,397; and Loken et al, U.S. Pat. No. 5,137,809, all of which are hereby incorporated by reference in their entirety.

As noted above, for example, an alpha 6 integrin-specific monoclonal antibody or an antibody for FGFR-1, Bcl-2, prominin, CD34, Notch or Fzd3 can be immobilized, such as on a column or on magnetic beads. The entire cell population may then be passed through the column or added to the magnetic beads. Those that remain attached to the column or are attached to the magnetic beads, which may then be separated magnetically, are those cells that contain a marker that is recognized by the antibody used. Thus, if the anti-alpha 6 integrin antibody is used, then the resulting population will be greatly enriched in alpha 6 integrin expressing cells. If the antibody used is to FGFR, then the resulting population will be greatly enriched in FGFR cells. That population may then be enriched in another marker by repeating the steps using a solid phase having attached thereto an antibody to the other marker.

Another way to sort alpha 6 integrin$^+$ cells, Sca-1$^+$ cells, FGFR$^+$ cells, prominin$^+$ cells, CD34$^+$ cells, Notch$^+$ cells and Frizzled protein$^+$ cells is by means of flow cytometry, most preferably by means of a fluorescence-activated cell sorter (FACS), such as those manufactured by Becton-Dickinson under the names FACScan or FACSCalibur. One can also sort for Bcl-2 cells but as Bcl-2 is not an extracellular antigen, cells will first have to be permeabilized to get the antibodies into the cells in a manner known to those of ordinary skill in the art.

By means of this technique, the cells having alpha 6 integrin or Sca-1 or other identifying proteins as a marker thereon are tagged with a particular fluorescent dye by means of an antibody to the antigen of interest, which has been conjugated to such a dye. When the stained cells are placed on the instrument, a stream of cells is directed through an argon (and/or helium neon) laser beam that excites the fluorochrome to emit light. This emitted light is detected by a photo-multiplier tube (PMT) specific for the emission wavelength of the fluorochrome by virtue of a set of optical filters. The signal detected by the PMT is amplified in its own channel and displayed by a computer in a variety of different forms, such as a histogram, dot display, or contour display. Thus, fluorescent cells which emit at one wavelength express a molecule that is reactive with the specific fluorochrome-labeled reagent, whereas non-fluorescent cells or fluorescent cells that emit at a different wavelength do not express this molecule but may express the molecule that is reactive with the fluorochrome-labeled reagent that fluoresces at the other wavelength. The flow cytometer is also semi-quantitative in that it displays the amount of fluorescence (fluorescence intensity) expressed by the cell. This correlates, in a relative sense, to the number of the molecules expressed by the cell.

Flow cytometers can also be used to measure non-fluorescent parameters, such as cell volume or light scattered by the cell as it passes through the laser beam. Cell volume is usually a direct measurement. The light scatter PMTs detect light scattered by the cell either in a forward angle (forward scatter) or at a right angle (side scatter). Forward scatter is usually an index of size, whereas side scatter is an index of cellular complexity, although both parameters can be influenced by other factors.

Preferably, the flow cytometer is equipped with more than one PMT emission detector. The additional PMTs may detect other emission wavelengths, allowing simultaneous detection of more than one fluorochrome, each in individual separate channels. Computers make it possible to analyze each channel or to correlate each parameter with another.

Fluorochromes which are typically used with FACS machines includes fluorescein isothiocyanate, which has an emission peak at 525 nm, R-phycoerythrin, which has an emission peak at 575 nm, propidium iodide, which has an emission peak at 620 nm, 7-aminoactinomycin D, which has an emission peak at 660 nm, R-phycoerythrin Cy5, which has an emission peak at 670 nm, and allophycocyanin, which has an emission peak at 655-750 nm.

Any other method for isolating or otherwise enriching the prostatic stem cells of the present invention with respect to a starting material may also be used in accordance with the present invention.

Using the techniques described herein, as well as others that are apparent to one skilled in the art, one can isolate cell populations that have a high degree of expression of the markers characterizing prostatic stem cells, as these cells have significantly greater proliferative capacity than cells isolated that do not have a high expression of these markers. By identifying if a patient has a higher than normal proportion of these prostatic stem cells, the patient may wish to have these cells ablated so as to prevent development of proliferative diseases, such as BPH and prostate cancer.

Other "primitive" phenotype indicators are known which can be used to distinguish the prostatic stem cells from cells that are not stem cells. Among these markers are Thy-1, CXCR4, Hedgehog (Karhadkar et al, 2004), c-kit and members of the Polycomb family, such as Bmi1 and EZH2 (Valk-Lingbeek et al, 2004; Varambally et al, 2002). It is possible that a study of these additional antigens will further stratify the prostatic stem cell phenotype. While the prostatic stem cells of the present invention can be isolated in substantial purity, i.e., in a substantially homogeneous population, by the methods described above, it is not always necessary that the stem cell population of the present invention be present in substantial purity. For example, for most purposes, it is sufficient if the population of cells are enriched in prostatic stem cells that contain alpha 6 integrin, or other markers indicating that the cells are indeed prostatic stem cells.

These antigens can be identified by conventional methods, such as by isolating a stem cell population expressing a particular stem cell marker, and injecting this isolated population to look for antibodies to hitherto unknown proteins expressed by these cells.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostatic stem cell or a variant thereof. Immunogenic portions may generally be identified using well-known techniques, such as those summarized in Paul (1993) and references cited therein. Such techniques include screening polypeptides for the ability to react with prostate carcinoma protein-specific antibodies, antisera and/or T-cell lines or clones. As used herein, antisera and antibodies are "prostate carcinoma protein-specific" if they specifically bind to a prostate carcinoma protein (i.e., they react with the prostatic carcinoma protein in an ELISA or other immunoassay, and do not react detectably with unrelated proteins). Such antisera, antibodies and T cells may be prepared using well-known techniques. An immunogenic portion of a native prostatic carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full-length protein. Such screens may generally be performed using methods well known to those of ordinary skill in the art, such as those described in Harlow et al (1988). For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

Proximal cells expressing Sca-1, alpha 6 integrin, Bcl-2, FGFR, prominin, CD34, Notch or Frizzled proteins, and combinations thereof, have significantly greater proliferative potential than cells without these antigens. The data presented in this application show that prostatic stem cells are concentrated in the proximal region of murine prostatic ducts and express Sca-1, alpha 6 integrin, Bcl-2, FGFR, prominin, CD34, Notch and Frizzled proteins on their surfaces. In view of this great proliferative potential of the prostatic stem cells and the knowledge with respect to other tumors that the most aggressive and proliferative portion of the tumor is the relatively small portion thereof that are solid tumor stem cells, it is expected that the prostatic tumor stem cell markers are also present on the stem cell portion of prostatic tumor cells and BPH cells. Thus, the present invention provides a way that anti-cancer therapies can be directed specifically against the prostatic tumor stem cells.

The previous failure of cancer therapies to significantly improve outcome has been due in part to the failure of these therapies to target the solid tumor stem cells within a solid tumor that have the capacity for extensive proliferation and the ability to give rise to all other solid tumor cell types. Effective treatment of prostatic tumors thus requires therapeutic strategies that are able to target and eliminate the tumorigenic subset of prostatic tumor cells, i.e., the solid prostatic tumor stem cells, by the direct targeting of therapeutics to the prostatic tumor stem cells.

In other words, there is a hierarchy of prostatic tumor cells in which only a fraction of the cells have the ability to proliferate extensively (the prostatic tumor stem cells), while other cells have only a limited proliferative potential. Phenotypically distinct populations of prostatic tumor cells have an intrinsically greater capacity to proliferate extensively and form new tumors than other populations. Thus, using the markers disclosed herein, one can predict whether cancer cells are tumorigenic or depleted of tumorigenic activity. If the non-tumorigenic cells are preferentially killed by particular therapies, then tumors may shrink, but the remaining tumorigenic cells will drive tumor recurrence. By focusing on the prostatic tumor stem cell population, which is the tumorigenic population, one can identify critical proteins that are expressed by virtually all of the tumorigenic cells in prostate cancer. The identification of the prostatic tumor stem cells allows the identification of more effective therapeutic targets, diagnostic markers that detect the dissemination of the prostatic tumor stem cells and more effective prognostic markers, by focusing on the tumorigenic cells rather than on more functionally heterogenous collections of prostate cancer cells.

Prostatic stem cells and prostatic stem cell progeny of the present invention can be used in methods of determining the effect of biological agents on prostatic tumor cells, e.g., for diagnosis, treatment or a combination of diagnosis and treatment. The term "agent" or "compound" refers to any agent (including a virus, protein, peptide, amino acid, lipid, carbohydrate, nucleic acid, nucleotide, drug, antibody, prodrug, other "biomolecule" or other substance) that may have an effect on prostatic tumor stem cells whether such effect is harmful, beneficial, or otherwise. The ability of various biological agents to increase, decrease, or modify in some other way the number and nature of the prostatic tumor stem cells and prostatic tumor stem cell progeny can be assayed by methods known to those of skill in the drug discovery art.

In another embodiment, a biomolecule or biological agent selectively targeted to a prostatic tumor stem cell can use gene therapy strategies. For example, the biomolecule can be a gene therapy suicide vector targeted to prostatic tumor stem cells using markers expressed by the prostatic tumor stem cells. In one embodiment, the vector is an adenoviral vector that has been redirected to bind to one or more of the markers described herein. Thus, for example, anti-fiber and alpha 6 integrin antibodies can be conjugated with the Prolinx (Prolinx, Inc., Bothell, Wash., USA) method (see Douglas et al, 1996). When the modified anti-knob and anti-alpha 6 integrin antibodies are mixed together, they became cross-linked and generated a bi-specific conjugate. The anti-fiber antibody part of the conjugate can bind to the adenovirus, while the anti-alpha 6 integrin moiety can bind to the prostate cancer stem cell. Incubation of the AdLacZ virus with the anti-fiber alone blocks the infectivity of the virus. The infectivity of virus incubated with the bi-specific conjugate is restored only in the cells that express high levels of the alpha 6 integrin antigen. The re-targeting is specific, because it can be inhibited by free alpha 6 integrin antibody. The conclusion is that a bi-specific conjugate can modify the infectivity of a vector, blocking its natural tropism and directing the infection to cells that express the prostatic tumor stem cell surface marker. See also Michael et al (1993).

The adenovirus vector can carry a vector with DNA encoding any cytotoxic or cytostatic agent. Once internalized into the targeted cell, the bound DNA will become activated within the cell. One aspect of the present invention is to internalize an agent that is specifically directed against transcription of the Bcl-2 polypeptide. Inhibition of Bcl-2 transcription will impair the growth of the prostatic tumor stem cells. The DNA sequence encoding Bcl-2 is known—see GenBank Accession No. M14745. Knowing this sequence appropriate anti-sense or RNAi sequences that will disrupt transcription of Bcl-2 can be readily designed by techniques well known in the art. It is expected that any molecule that interferes with the transcription of Bcl-2 will change the phenotype of a stem cell and prevent its further proliferation. As long as the cytotoxic or cytostatic therapeutic agent can be targeted directly to the prostatic tumor stem cells, the chance of further aggressive growth or metastasis is greatly diminished.

Inhibitors of Notch signaling (such as Numb and Numb-like; or antibodies or small molecules that block Notch activation) can be used in the methods of the invention to inhibit solid tumor stem cells. In this manner, the Notch pathway is modified to kill or inhibit the proliferation of solid tumor stem cells. See WO 03/050502.

Another way to target a vector specifically to prostate tumor stem cells is by use of a multipurpose antibody derivative, such as those described in Schoonjans et al, U.S. Pat. No. 6,809,185, which is hereby incorporated herein by reference. This patent teaches how to make multifunctional antibody derivatives that can recognize two or more specific cell surface antigens and still be conjugated to a therapeutic moiety active when internalized into the targeted cells. By targeting two or more of the cell surface markers that designate prostate tumor stem cells and then acting only on an internal peptide that is another prostate tumor stem cell marker, the therapy becomes highly selective. This is particularly the case if injected directly into the prostatic tumor.

One skilled in the oncological art can understand that the vector is to be administered in a composition comprising the vector together with a carrier or vehicle suitable for maintaining the transduction or transfection efficiency of the chosen vector and promoting a safe infusion. Such a carrier may be a pH balanced physiological buffer, such as a phosphate, citrate or bicarbonate buffer in a saline solution, a slow release composition and any other substance useful for safely and effectively placing the targeted agent in contact with solid tumor stem cells to be treated.

Depending on the specific conditions being treated, agents may be formulated and administered systemically or locally. Techniques for formulation and administration may be found in *Remington's Pharmaceutical Sciences* (2000). Suitable routes may include oral, rectal, transdermal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few. The agents may also be injected directly into the prostate, preferably guided by an appropriate imaging technique, such as ultrasound.

For injection, the agents of the invention may be formulated in aqueous solutions, preferably in physiologically compatible buffers such as Hanks solution, Ringers solution, or physiological saline buffer. For such transmucosal administration, penetrants appropriate to the barrier to be permeated are used in the formulation. Such penetrants are generally known in the art.

In addition to the active ingredients, these pharmaceutical compositions may contain suitable pharmaceutically acceptable carriers comprising excipients and auxiliaries, which facilitate processing of the active compounds into preparations that can be used pharmaceutically. The preparations formulated for oral administration may be in the form of tablets, capsules, or solutions. The pharmaceutical compositions of the present invention may be manufactured in a manner that is itself known, e.g., by means of conventional mixing, dissolving, granulating, levigating, emulsifying, encapsulating, entrapping or lyophilizing processes. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

The exact formulation, route of administration and dosage can be chosen by the individual physician in view of the patient's condition (see, e.g., Fingl et al, 1975). The attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the clinical disorder of interest can vary with the severity of the condition to be treated and the route of administration. See, Budavari et al (1996); Walsh (2000). The severity of the condition may, for example, be evaluated, in part, by appropriate prognostic evaluation methods. Further, the dose and perhaps dose frequency, also vary according to the age, body weight, and response of the individual patient. A program comparable to that discussed above may be used in veterinary medicine.

The presence and relative ratio of prostatic tumor stem cells found, for example in a biopsy of a prostate tumor, will directly relate to the aggressiveness and thus the danger of the particular tumor being tested. Histology will determine the presence of a tumor. However, by means of the markers disclosed herein, the ratio of prostatic tumor stem cells among the tumor cells can be determined by means that would be well known to those of ordinary skill in the art, including RT-PCR, flow cytometry, etc. Binding agents that are capable of binding only to cells having a plurality of specified markers would be preferably used for the purpose of the present invention in order to target only to the prostatic stem cells. See U.S. Pat. No. 6,809,185. Such binding agents, preferably bivalent or multivalent binding agents, may be used in assays that are capable of differentiating between patients with and without prostate cancer or BPH. In other words, antibodies or other binding agents that bind to a prostate cancer stem cell antigen or, more preferably, a combination thereof, will be expected to generate a signal indicating the presence of a cancer in at least about 20% of patients with the disease, and will generate a negative signal indicating the absence of the disease in at least about 90% of individuals without the cancer. In a contained tumor, one would not expect to see these markers in the urine or the blood of a patient. However, if the tumor is metastasizing, then prostate tumor stem cells, or the free DNA thereof, may circulate and be found in the circulating bloodstream. Thus, a sensitive RT-PCR may be used to find DNA encoding the markers of the present invention so as to determine from the blood or serum, or even the urine, of a patient whether his prostate tumor has metastasized.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow et al (1988). In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler et al (1976), and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density in a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow et al, 1988) and digested by papain to yield Fab and Fc fragments. The Fab and Fc fragments may be separated by affinity chromatography on protein A bead columns.

Monoclonal antibodies of the present invention may be used alone to treat proliferative prostate diseases, or they may be coupled to one or more therapeutic agents. Suitable agents in this regard include radionuclides, differentiation inducers, drugs, toxins, and derivatives thereof. Preferred radionuclides for therapy and detection include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diphtheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other. A leaving group is one that is pushed off when the new group reacts with the moiety.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group that is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al), by hydrolysis of derivatized amino acid side chains (e.g., U.S. Pat. No. 4,638,045, to Kohn et al), by serum complement-mediated hydrolysis (e.g., U.S. Pat. No. 4,671, 958, to Rodwell et al), and acid-catalyzed hydrolysis (e.g., U.S. Pat. No. 4,569,789, to Blattler et al).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers that provide multiple sites for attachment can be used. Alternatively, a carrier can be used. A carrier may bear the agents in a variety of ways, including covalent bonding either directly or via a linker group. Suitable carriers include proteins such as albumins (e.g., U.S. Pat. No. 4,507,234, to Kato et al), peptides and polysaccharides such as aminodextran (e.g., U.S. Pat. No. 4,699,784, to Shih et al). A carrier may also bear an agent by non-covalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al discloses representative chelating compounds and their synthesis.

It is also possible to use one or more antibodies to one or more antigens expressed by the prostatic stem cells to inhibit proliferation of these cells.

A variety of routes of administration for the antibodies and immunoconjugates may be used. Typically, administration will be intravenous, intramuscular, subcutaneous, in the bed of a resected tumor, or directly injected into the tumor without resection using an imaging technique. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of a prostatic carcinoma protein. Such antibodies may be raised against an antibody, or antigen-binding fragment thereof, that specifically binds to an immunogenic portion of a prostatic carcinoma protein, using well known techniques. Anti-idiotypic antibodies that mimic an immunogenic portion of a prostatic carcinoma protein are those antibodies that bind to an antibody, or antigen-binding fragment thereof, that specifically binds to an immunogenic portion of a prostatic carcinoma protein, as described herein.

Materials and Methods

Cell Preparation and FACS Analysis

The dorsal, ventral and lateral prostates were removed from six-week-old C57BL/6 mice and dissected into two regions: (1) the proximal region that includes those ducts nearest the urethra and (2) the remaining region that includes the intermediate and distal cell ducts. Cell digests (Tsujimura et al, 2002) were suspended in FACS buffer (phosphate buffered saline containing 0.1% bovine serum albumin, 0.01% sodium azide and 20 micrograms/ml aprotinin). Fc receptors were blocked with mouse CD16/32 antibodies and rat IgG for ten minutes on ice. The cells were then incubated in the presence of antibody or control IgG for 30 minutes and washed twice with FACS buffer. In some experiments, the dye 7-aminoactinomycin D (7-AAD) was added five minutes prior to analysis at a final concentration of 1 microgram/ml, so that dead cells could be excluded from analysis. Bcl-2 expression was determined in paraformaldehyde fixed cells, permeabilized with Tween20.

Antibodies to Sca-1, conjugated to phycoerythrin (PE), fluorescein isothiocyanate (FITC) or biotin/SA-APC were used in conjunction with antibodies to alpha 6 integrin conjugated to FITC or antibodies to Bcl-2 conjugated to PE, in order to determine the incidence of co-expression of Sca-1 and these antigens. As PE has a higher intensity than FITC or APC, cells with mean fluorescence intensity (MFI) greater than 1000 for Sca-1 PE or greater than 200 for Sca-1 FTIC or Sca-1 biotin plus streptavidin APC were considered to express high levels of Sca-1 (Sca-1$^{high}$). FACS analysis of cells co-expressing Sca-1, prominin and FGFR-1 was performed using antibodies to Sca-1 conjugated to PE, antibodies to FGFR-1 conjugated to APC and biotinylated antibodies to prominin, followed by streptavidin FITC. Expression of CD34 by prostatic cells was assayed using antibodies to CD34 conjugated to PE. Analysis of Sca-1$^+$/Frizzled3$^+$ cells was performed using rat-anti Frizzled3 antibodies, biotinylated rabbit anti-rat antibodies, streptavidin-APC and Sca-1 conjugated to PE. Analysis of Notch1 was performed using PE-labeled antibody to this protein. Cells were analyzed on a FACSCalibur flow cytometer (Becton-Dickinson, San Jose, Calif.) using CellQuest software (Becton-Dickinson, San Jose, Calif.).

Implantation of Grafts Under the Renal Capsule

Cells ($1\times10^5$ or $3\times10^4$) from different regions of prostatic ducts were combined with urogenital sinus mesenchyme (UGM) cells ($2\times10^5$) and resuspended in 30 microliters of Type 1 collagen (BD Biosciences, Bedford, Mass.). The collagen grafts were inserted under the renal capsule (Cunha et al, 1987b). Each experiment contained grafts of UGM alone to insure that tissue growth did not result from contaminating urogenital sinus epithelial cells. The grafts were harvested and weighed after eight to ten weeks of in vivo growth. UGM was isolated from the urogenital sinus of 18-day-old embryos from CDIGS rats (Cunha et al, 1987b; Norman et al, 1986). Fetal rat UGM was used in place of fetal mouse UGM, as the rat UGM promotes growth more effectively than mouse UGM (Norman et al, 1986).

Isolation of Sca-1 and Alpha 6 Integrin Expressing Cells

Prostatic duct digests were enriched for Sca-1 expressing cells by immunomagnetic separation, using magnetically activated cell sorter (MACS) microbeads coated with antibodies to Sca-1, magnetic columns and the MiniMACS system (Miltenyi Biotec, Auburn, Calif.). Alpha 6 integrin expressing cells were isolated using antibodies to this protein and the MACS technology as above. In some experiments, Sca-1 expressing cells were sorted by FACS into various fractions: Sca-1$^{high}$, Sca-1$^{med/low}$, or Sca-1$^{negative}$ according to the MFI of Sca-1 expression by the cells.

Statistical Analysis

The results are depicted as the means and standard deviation of each set of data. Comparisons between groups of data were made using the 2-tailed, paired Student's t test, or in the case of different sized samples, the Mann Whitney U test. A p value of <0.05 is considered statistically significant.

Preparation of Dissociated Prostate and Urethra Cells 6-week-old C57BL/6 mice were killed by cervical dislocation and the urogenital tract was removed en bloc and transferred in Hanks balanced salt solution (HBSS) (Mediatech, Herndon, Va.). The dorsal prostate of 6-week-old mice was removed and dissected under a dissecting microscope in the presence of 0.5% collagenase (Sigma-Aldrich, St. Louis, Mo., 1.3 units/mg) (Sugimura et al, 1986a). The proximal, intermediate and distal regions were excised, minced finely and incubated in collagenase for 60 minutes followed by digestion in 0.25% trypsin (Difco, Livonia, Mich.) for a further 10 minutes at 37° C. (Tsujimura et al, 2002). A portion of the urethra was removed and digested similarly. Cells were passed through a 40 µm nylon mesh (Becton Dickinson, Franklin Lakes, N.J.) and viability was determined by trypan blue exclusion.

Preparation of Urogenital Sinus Mesenchyme (UGM) Cells

Urogenital sinus mesenchyme (UGM) was isolated from the urogenital sinus of 18-day-old embryos from CDIGS rats following digestion with trypsin (1%) at 4° C. for 90 minutes (Cunha et al, 1987a; Norman et al, 1986). A single cell suspension of UGM cells was obtained by digesting the UGM tissue for 10 minutes at 37° C. in collagenase (0.5%). Fetal rat UGM was used in place of fetal mouse UGM as rat UGM promotes growth more effectively than mouse UGM (Norman et al, 1986).

Implantation of Grafts Under the Renal Capsule

The grafts were implanted under the renal capsule of intact or castrated athymic male mice (Cunha et al, 1987a) (tutorial for technique: "mmmary.nih.gov/tools/Cunha001/index.html".) Cells from the urethra or different regions of ducts ($1 \times 10^5$ unless otherwise indicated) were combined with UGM cells ($2.5 \times 10^5$) and resuspended in 30 µl of type 1 collagen (BD Biosciences, Bedford, Mass.). The collagen was allowed to gel at 37° C. for 15 minutes after which the grafts were inserted under the renal capsule. Where indicated, androgens were administered by the subcutaneous implantation of testosterone pellets (Innovative Research of America, Sarasota, Fla.). Each experiment contained grafts of UGM alone ($3.5 \times 10^5$ cells) to insure that tissue growth did not result from contaminating urogenital sinus epithelial cells. In addition some experiments were done using prostate cells isolated from GFP transgenic mice (C57BL/6-TgN, The Jackson laboratory, Bar Harbor, Me.) to insure that tissue growth resulted from donor GFP-expressing cells and not contaminating epithelial cells in the UGM preparation. Grafts were harvested after 8 weeks of in vivo growth, weighed and used for immunohistochemical examination.

Passage of Undissected Recombinant Tissue (All Regions) In Vivo

Figure 6:
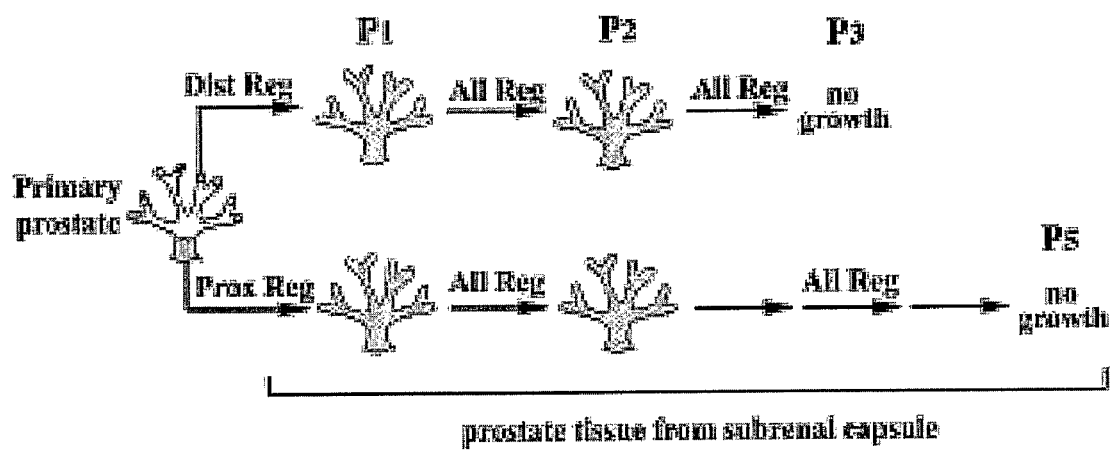
FIG. 6A is a schematic diagram showing the protocol used for passaging proximal and distal cells isolated from primary prostate tissue. Proximal and distal cells ($10^5$) were combined with UGM cells ($2.5\times10^5$) and implanted under the renal capsule of intact animals. Grafts arising from proximal and distal cells were harvested after eight weeks, digested with collagenase, and cells ($10^5$) from each type of graft were again combined with UGM cells ($2.5\times10^5$) and implanted under the renal capsule for an additional eight weeks. This process was repeated until no further tissue growth was noted.
FIG. 6B shows the weights of tissues arising from proximal and distal cells at each passage.
Figure 6:
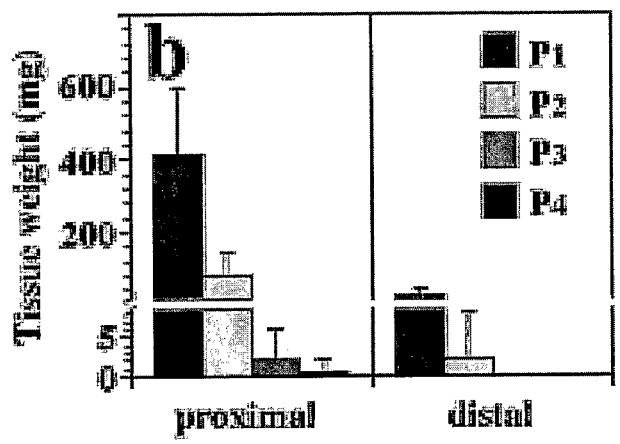

The ability of proximal and distal regions of primary prostate cells to undergo multiple rounds of growth was assessed by serial in vivo passaging of recombinant tissue. Cells isolated from proximal and distal regions of prostatic ducts ($1 \times 10^5$) were combined with UGM ($2.5 \times 10^5$ cells) and implanted under the renal capsule of intact 6-week-old male athymic nude mice. After 8 weeks, the recipient mice were sacrificed, and grafts from either proximal or distal cells (P1) (FIG. 6A) were retrieved and weighed. Grafts arising from either proximal or distal cells were minced finely, digested in collagenase (see above) and Trypan blue excluding cells were enumerated. These cells ($1 \times 10^5$ cells) were combined with UGM ($2.5 \times 10^5$ cells) and implanted into recipient mice to produce a "second passage (P2)" graft (FIG. 6A). This protocol was repeated until no tissue growth was noted (four passages for cells removed from proximal regions vs two passages for distal cells, FIG. 6B).

Passage of the Proximal Region of Recombinant Tissue In Vivo

Figure 7:
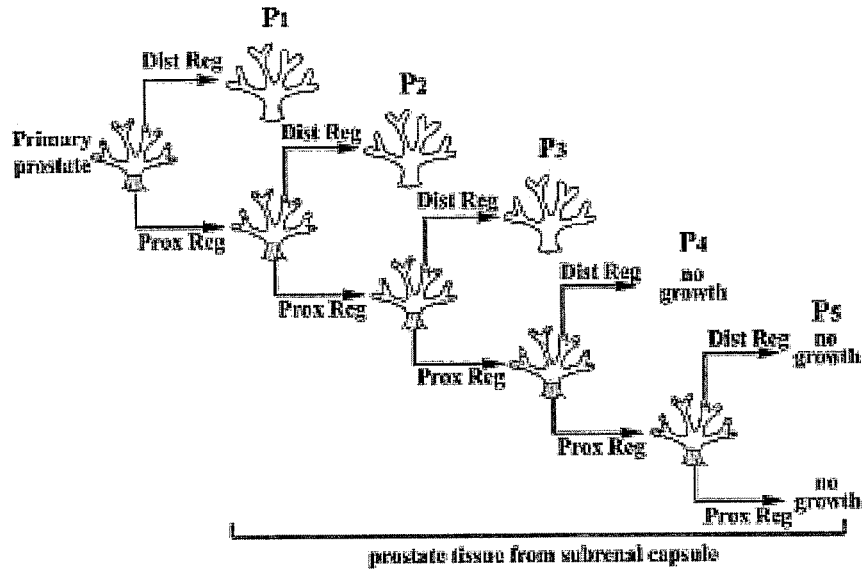
FIG. 7A is a schematic diagram showing the protocol used for passaging proximal and distal cells isolated from recombinant tissue. Proximal and distal cells ($10^5$) were isolated after collagenase digestion of successive passages of sub-renal capsule tissue. Digests of successive passages of subrenal capsule tissue were combined with UGM cells (2.5× $10^5$) and implanted under the renal capsule of intact animals until no further tissue growth was noted.
FIG. 7B shows the morphology of the prostatic ductal system of a collagenase digested lobe of the dorsal prostate showing the proximal (prox) and distal (dist) regions of ducts.
FIG. 7C shows the morphology of the prostatic ductal system of collagenase digested recombinant prostate tissue arising from proximal cells showing the proximal (prox) and distal (dist) regions of ducts. This indicates that the recombinant tissue has the same morphology and proximal-distal axis as a primary prostate.
FIG. 7D shows weight of tissue arising from each passage of proximal and distal cells obtained from the recombinant tissue, weighed at each successive passage. This indicates that cells in the proximal region of recombinant tissue have greater proliferative potential than cells in the distal region.
Figure 7:
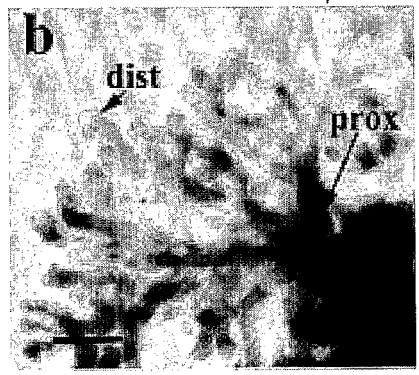
Figure 7:
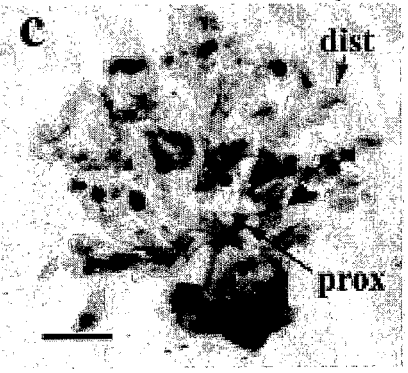
Figure 7:
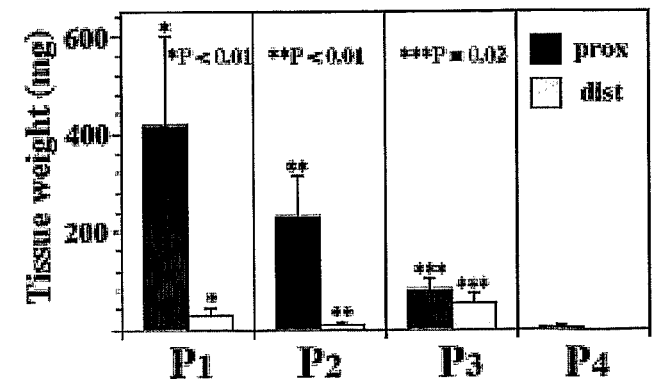

Sub-renal capsule grafts from cells isolated from the proximal region were digested with collagenase (see above) and revealed a ductal network similar to that observed in a prostate removed from an animal (P1, FIGS. 7B-7C). To determine if the sub-renal capsule grafts maintained a proximal-distal axis and to ascertain if cells within the proximal and distal regions of these grafts exhibited the differential growth capacity of proximal and distal cells isolated from a 'primary' prostate (FIG. 7A), the recombinant tissue arising from proximal cells was dissected into proximal and distal regions. Single cell suspensions of these regions were prepared (see above) and proximal and distal cells ($1 \times 10^5$) were combined with UGM ($2.5 \times 10^5$ cells) and implanted into a second generation of recipient animals to produce a "second passage (P2)" graft (FIG. 7A). The proximal region of this P2 graft was again dissected into proximal and distal regions and the proximal region passaged as above into a third generation of recipient animals (P3, FIG. 7A). This protocol was repeated until no tissue growth was observed (FIG. 7A). After each tissue passage animals were sacrificed after 8 weeks of in vivo growth and grafts were removed and weighed.

Immunohistochemistry

Grafts were fixed in 70% ethanol or 3% paraformaldehyde and embedded with paraffin and sections were stained with hematoxylin and eosin. Immunohistochemistry was performed as described previously (Salm et al, 2002; Takao et al, 2003). Mouse monoclonal antibodies to cytokeratin 8 (Research Diagnostics Inc, Flanders, N.J.) and alpha-smooth muscle actin (Sigma-Aldrich, St. Louis, Mo.) were directly coupled to horse radish peroxidase (HRP) using Dako's Envision+system (Dako, Carpinteria, Calif.) and detected using DAB as the substrate. Rabbit polyclonal antibodies that are specific to secretions of the dorsal prostate were a gift of Dr C. Abate-Shen (Robert Wood Johnson Medical School, Piscataway, N.J.; M. Kim, M. M. Shen, and C. Abate-Shen, personal communication (Tsujimura et al, 2002). Cytokeratin 5 was visualized using rabbit polyclonal antibodies (Covance, Berkeley, Calif.) and appropriate HRP-linked secondary antibodies (Amersham Biosciences Corp, Piscataway, N.J.). The specificity of staining was ascertained on sections using non-immune serum or IgG in place of primary antibodies. Sections were counterstained with hematoxylin.

EXAMPLE 1

Isolated Single Cell Populations Obtained from Prostatic Tissue Form Large Amounts of Prostatic Tissue Under the Renal Capsule The mouse prostate can be divided into ventral, dorsal and lateral lobes, each of which contains an arborizing network of ducts that consist of a proximal region (adjacent to the urethra), an intermediate region and a small distal region (Sugimura et al, 1986a; Kinbara et al, 1996). Cells were isolated from each of these regions of the dorsal prostate (DP), from a pool of all regions together and from the urethra (FIG. 1A) and the same number of cells ($10^5$) were combined with embryonic rat UGM cells ($2.5 \times 10^5$) and their proliferative capacity determined by measuring the size of tissue grafts 8 weeks after implantation under the renal capsule (RC) (FIGS. 1A-1B). Cells isolated from the proximal region of the prostate form significantly more prostatic tissue (417±180 mg) than cells isolated from the intermediate (65±26 mg; p<0.001) or distal regions (25±19 mg; p<0.001) or cells isolated from the entire gland comprising all regions (226±147 mg; p<0.001). This indicates that, within the prostate, the cells with the greatest proliferative potential reside in the proximal region of prostatic ducts and that cells within the urethra also form large amounts of prostatic tissue in vivo (352±154 mg).

Interestingly, when urethral cells were isolated from a female animal and combined with UGM, no tissue growth was noted, indicating that the ability of urethral cells to form prostatic tissue was a property of the male urethra. Cells from the proximal region form 17-fold more tissue than cells from the distal region (FIGS. 1B-1D) and give rise to prostatic tissue that is 38-fold larger than that of a normal prostate in situ (11.0±1.1 mg for DP). Histology revealed a complex ductal network indistinguishable from normal prostate, containing basal (FIG. 1E) and luminal (FIG. 1F) cells with secretory material (FIG. 1G) in the ductal lumens. The histological composition of tissue arising from proximal and distal cells was similar. Proximal cells from Green Fluorescent Protein (GFP)-expressing mice were used to verify that the tissue was from engrafted proximal cells and not from contaminating epithelial cells from the fetal urogenital sinus (data not shown) which are removed during the preparation of the UGM. In addition, the absence of contaminating fetal epithelial cells was verified in each experiment by including sub-renal capsule grafts of UGM cells alone.

Figure 2A:
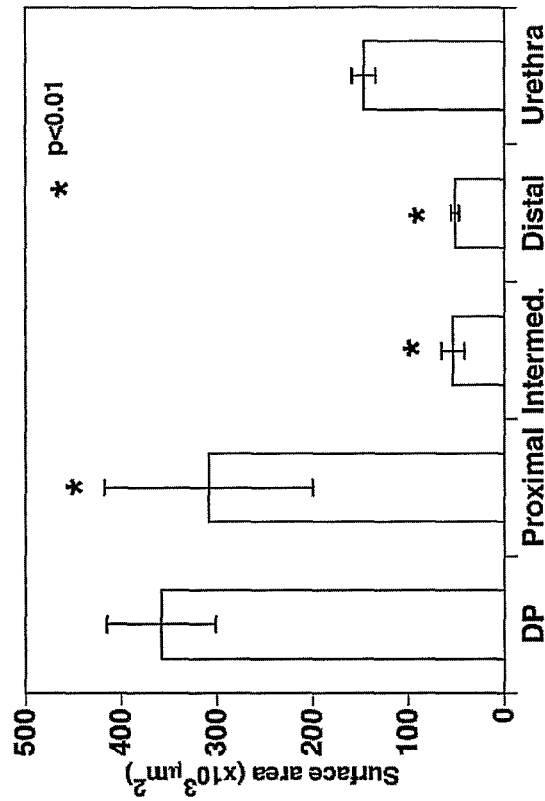
FIG. 2 shows that proximal cells form large glandular structures in collagen gels in vitro.
Figure 2B:
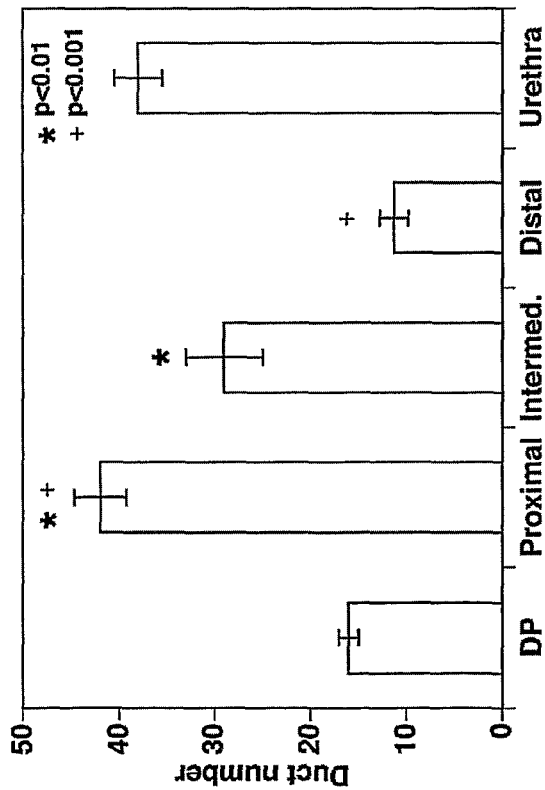

As it has previously been shown that cells from the proximal region form more, large branched glandular structures in collagen gels than those isolated from the distal region (Tsujimura et al, 2002), the ability of each population of cells studied in vivo to form glandular ducts when suspended in collagen gels in vitro (FIG. 2) was compared. Proximal cells gave rise to the most ducts, distal cells to the fewest ducts and cells from the intermediate region and the urethra formed ducts at a rate between that noted for proximal and distal cells (FIG. 2). Ducts formed by cells from the proximal region were larger ($148\pm24\times10^3$ $\mu m^2$) than those formed by cells from the urethra ($85\pm20\times10^3$ $\mu m^2$), the intermediate ($74\pm16\times10^3$ $\mu m^2$) or the distal region ($19\pm6\times10^3$ $\mu m^2$). This indicates that the ability of cells to form ducts in collagen gels in vitro approximates their capacity to form prostatic tissue in vivo.

Figure 3:
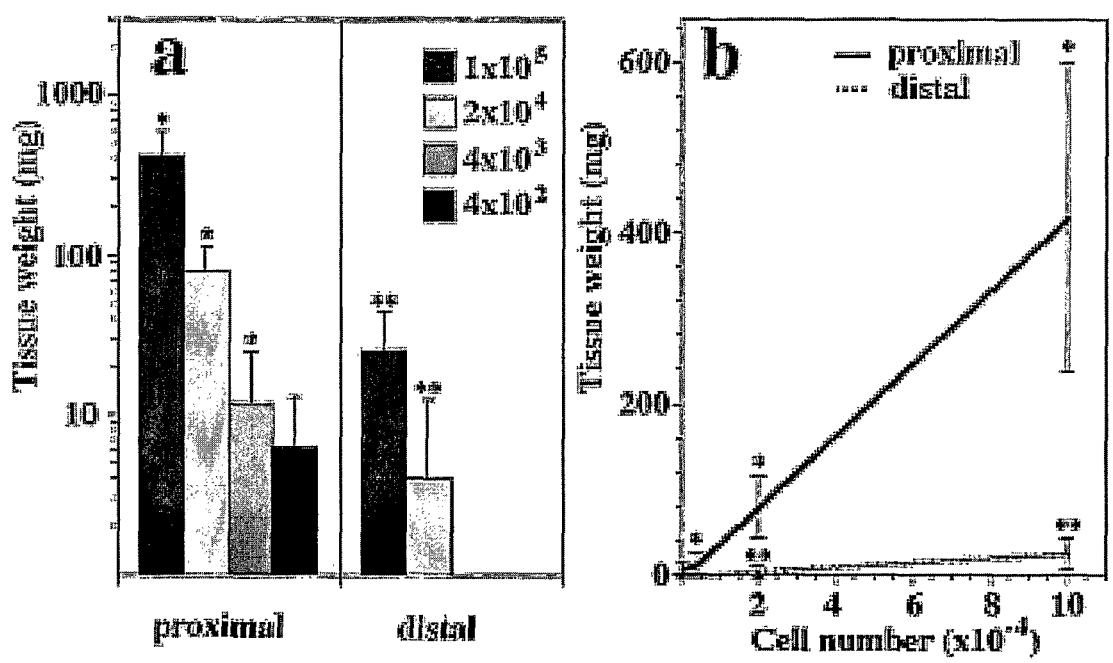
FIG. 3 shows the result when different numbers of proximal or distal cells ($10^5$ to $4\times10^2$) were combined with $2.5\times10^5$ UGM cells and implanted under the renal capsule. The grafts were harvested after eight weeks and weighed.

To determine the minimum number of cells capable of forming prostatic tissue in vivo, decreasing numbers of proximal and distal cells ($1.0\times10^5$-$4\times10^2$ cells) were combined with UGM cells ($2.5\times10^5$) and sub-renal capsule grafts were harvested after 8 weeks (FIGS. 3A-3B). Cells isolated from the proximal region contained 50-fold more stem cells or contained cells with 50-fold greater proliferative capacity than those from the distal region as 400 proximal cells formed prostatic tissue whereas 20,000 distal cells were required for tissue growth. A linear relationship between the tissue mass and inoculum dose was noted between 400 and $10^5$ cells (FIG. 3B). The size of the UGM inoculum also affected tissue size with a linear relationship in its ability to support prostate tissue growth between $2.5\times10^4$-$2.5\times10^5$ UGM cells (data not shown). The addition of $10^6$ UGM cells increased tissue mass approximately 52% over that noted for $2.5\times10^5$ cells. As the numbers of UGM cells are limited by the numbers of 18-day-old rat fetuses (approximately $2.5\times10^5$ UGM cells/fetus), $2.5\times10^5$ UGM cells were used for all experiments.

The above provides convincing evidence that prostatic stem cells are located in the proximal region of mouse prostatic ducts as well as in the male urethra. Cells isolated from these regions have significantly greater proliferative capacity in vivo than cells isolated from the intermediate or distal regions of ducts. As few as 400 isolated proximal cells form prostatic tissue whereas 20,000 distal cells are required, indicating that proximal cells are 50-fold more potent at forming prostatic tissue than distal cells.

EXAMPLE 2

Figure 4:
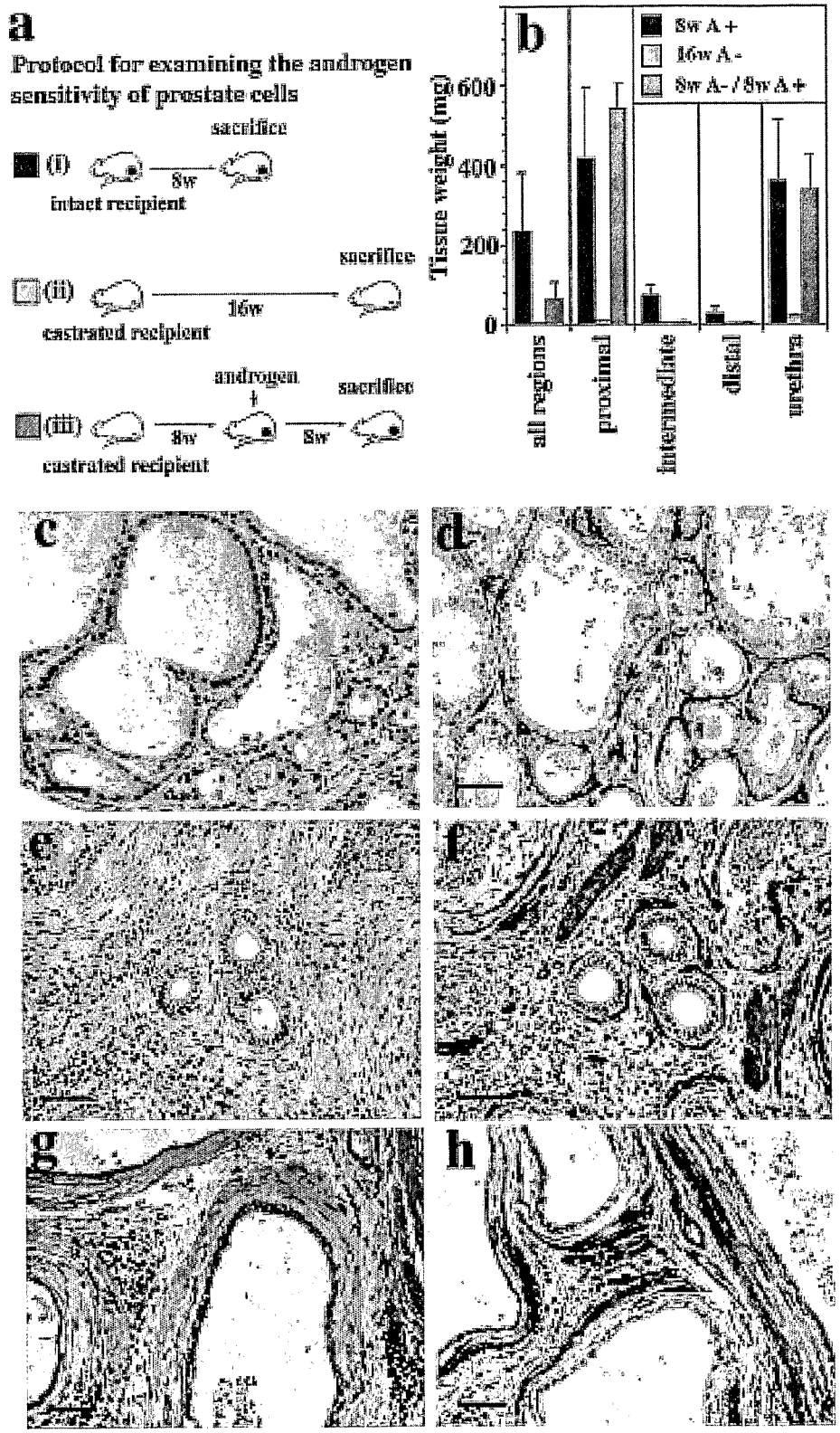
FIG. 4 shows that cells from the proximal region and the urethra survive prolonged androgen deprivation.
Figure 5:
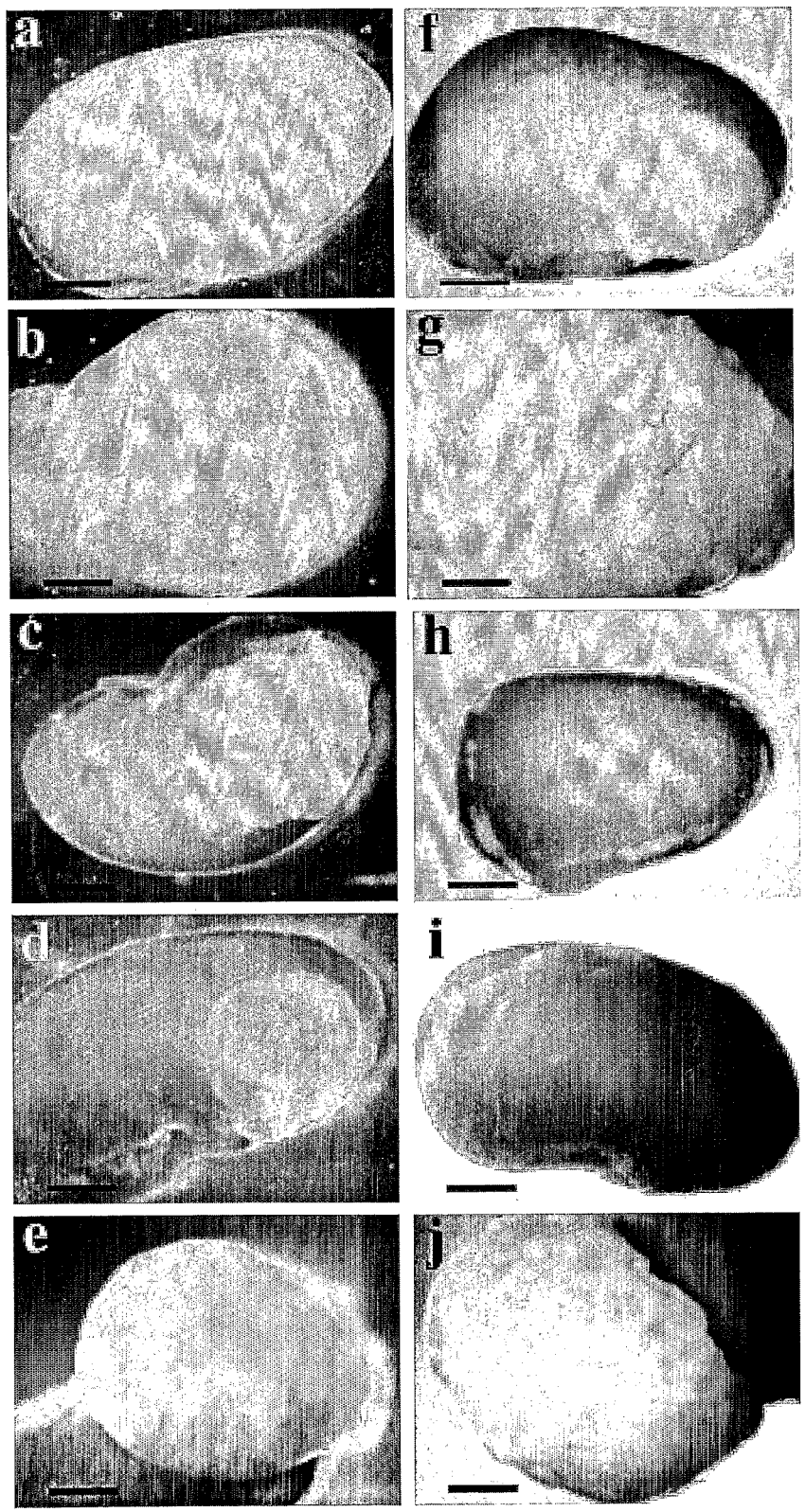
FIG. 5 shows that cells from the proximal region and the urethra survive prolonged androgen deprivation.

Cells from the Proximal Region and the Urethra Survive Prolonged Androgen Deprivation Prostatic stem cells are able to survive prolonged periods of androgen deprivation, as involuted prostates retain their ability to regenerate normally in vivo after androgen administration. Experiments indicated that the sub-renal capsule tissue was androgen sensitive, as it diminished by 67% after two weeks of androgen ablation (data not shown). It was therefore reasoned that the cell suspensions from regions most enriched in stem cells would survive prolonged androgen deprivation and regenerate prostatic tissue under the renal capsule (RC) to a greater extent than cells isolated from regions that consisted mainly of transit-amplifying or more differentiated cells. The transit-amplifying cells are progenitor cells capable of division and represent a post stem cell compartment. Three groups of mice were used to determine the sensitivity of cells isolated from different regions to androgens (FIG. 4A)—(i) intact, androgen replete recipients that received RC grafts for 8 weeks, (ii) castrated recipients that received RC grafts for 16 weeks and (iii) castrated recipients that received RC grafts for 8 weeks followed by androgen supplementation for an additional 8 weeks. Each group of mice received implants of cells ($10^5$) isolated from one of the following—all regions of ducts, the proximal, the intermediate or the distal region or the urethra. Very little growth was noted when cells from any region were implanted in castrated recipients (FIG. 4B, center bar in each group). Cells isolated from both the proximal region and the urethra were capable of surviving 8 weeks of androgen deprivation as the amount of prostatic tissue that was regenerated after subsequent exposure to androgens (FIGS. 4B, 5G and 5J) was comparable to that noted when cells from the proximal region (FIGS. 4B and 5B) or the urethra (FIGS. 4B and 5E) were implanted in intact animals. In contrast, the ability of cells isolated from the intermediate and distal regions to regenerate prostatic tissue was severely compromised by androgen deprivation (FIGS. 4B, 5H and 5I) indicating that these regions contained cells that required androgen for survival. Intermediate cells formed 65±26 mg tissue in intact animals (FIGS. 4B and 5C) compared with 5±3 mg (p<0.001) (FIGS. 4B and 5H) of tissue when cells were inoculated into animals maintained in an androgen-deficient environment for 8 weeks and subsequently exposed to androgens for an additional 8 weeks. Similarly most distal cells failed to survive 8 weeks of androgen deprivation (FIGS. 4B and 5D vs. FIG. 5I). Distal cells formed 25±19 mg tissue in the presence of androgens compared with 3±1 mg (p<0.001) after 8 weeks of deprivation followed by 8 weeks of androgen exposure indicating that cells capable of forming prostatic tissue did not survive the period of androgen ablation. Cells representative of all regions of the prostate formed 226±147 mg tissue in intact animals (FIGS. 4B and 5A) and could regenerate more prostatic tissue (62±46 mg; p<0.001) (FIGS. 4B and 5F) than intermediate or distal cells after androgen deprivation followed by androgen supplementation. It is likely that the tissue growth that followed androgen deprivation and supplementation in this sample was due to the proximal cells included in this fraction. These data indicate that cells with stem cell properties, namely those that are capable of surviving prolonged periods of androgen deprivation, are concentrated in the proximal regions of prostatic ducts and in the urethra.

The tissue formed from cells isolated from the distal and intermediate regions of ducts may arise from transit-amplifying cells rather than small numbers of stem cells, as neither distal nor intermediate cells were capable of surviving a prolonged period of androgen deprivation whereas proximal and urethral cells could readily regenerate prostate tissue when androgens were administered after a lengthy period of androgen ablation.

Histological examination of the tissue removed from intact animals showed prostatic ducts containing basal and luminal cells producing secretory material (FIGS. 1E-1H and 4C). The ducts were enveloped by a thin band of smooth muscle (FIG. 4D) as is noted in normal prostate (Nemeth et al, 1996). When implants of either intermediate or distal cells were placed in androgen-deprived animals, no evidence of epithelial cells or ducts was noted. However, when the implants of androgen deprived animals that received either isolated proximal or urethral cells were examined, small rudimentary epithelial ducts were noted 16 weeks after androgen deprivation. This indicates that some epithelial cells survived for prolonged periods in the absence of androgen and that these epithelial cells could form small ductal structures in the absence of androgen (FIGS. 4E and 4F). A significant amount of smooth muscle was noted in the surrounding stromal tissue (FIG. 4F). These ducts are the likely source of the stem cells from which the proximal and urethral tissue regenerated following androgen administration. Cells isolated from the urethra formed prostatic tissue with a similar histological and immunocytochemical profile to that noted for proximal cells. A few ducts were also noted in implants from cells isolated from 'all regions'. These ducts were most likely formed from the proximal cells contained within this preparation. Histological examination of the proximal and urethral tissues after androgen deprivation and subsequent regeneration indicated an extensive ductal network surrounded by significantly more smooth muscle tissue (FIG. 4H) than that which was noted in intact animals (FIG. 4D). The histological appearance and the amount of smooth muscle in the prostatic tissue of intact recipients was similar to that noted when implants were inserted in castrated animals that were immediately supplemented with androgens (data not shown). This indicates that the exogenously administered androgens were not responsible for the increased smooth muscle tissue. The increase in smooth muscle was only noted in those animals that experienced androgen ablation followed by an androgen supplementation and was not present in animals that were constantly exposed to steady levels of androgens.

These data show that the proximal region is enriched in cells with high proliferative potential. These cells are able to regenerate normal prostate tissue that maintains a proximal-distal axis for 3-4 consecutive passages in vivo. The tissue that is generated is androgen sensitive as it involutes following androgen withdrawal. The proximal region contains cells whose survival is not dependent on androgens as they can regenerate prostatic tissue after a prolonged period of androgen deprivation.

Cells isolated from the urethra of male mice form similar amounts of prostatic tissue as those from the proximal region of prostatic ducts whereas urethral cells from female mice do not grow in vivo. As urethral and bladder epithelium have previously been shown to form prostatic tissues when combined with UGM (Donjacour et al, 1993), and as it has been shown that urethral and proximal prostate cells both form equivalently large amounts of prostatic tissue under the renal capsule, it is possible that prostate, bladder and urethra may harbor a common stem cell that can give rise to all three tissues. The isolation of a possible common stem cell will depend on the definition of a specific stem cell phenotype and the development of specific assays to determine the potential of this population to develop into urethral, prostate and bladder epithelium.

EXAMPLE 3

Cells from the Proximal Region can be Serially Passaged In Vivo

Passage of Cells Isolated from Undissected Recombinant Tissue (i.e., All Regions)

As stem cells have a high proliferative potential, experiments were conducted to determine if the subrenal capsule tissue obtained after implantation of isolated proximal cells could be serially passaged in vivo more frequently than tissue arising from distal cell implantation.

Cells were isolated from the proximal and distal regions of dissected primary prostates and implanted ($10^5$) under the RC of intact recipient animals (FIG. 6A). Kidneys were removed from sacrificed animals after 8 weeks and the prostatic tissue from proximal and distal cell implants was removed, weighed and digested and cells ($10^5$) from proximal and distal digests were combined with UGM ($2.5\times10^5$ cells) and re-implanted under the RC for an additional 8 weeks. This process was repeated until no prostatic tissue growth was noted (FIGS. 6A and 6B).

Cells from the proximal region can be serially passaged in this manner four times whereas cells isolated from the distal regions of ducts can be passaged twice. In addition, as noted previously in primary implants (FIGS. 1 and 3-5) cells originally isolated from the proximal region formed larger amounts of prostatic tissue at each consecutive passage than cells originally isolated from the distal regions of ducts. This indicates that cells from the proximal region contain cells with a high proliferative capacity that can be serially passaged four times in vivo.

Passage of Cells Isolated from the Proximal Region of Recombinant Tissue In Vivo Sub-renal capsule grafts from cells isolated from the proximal region were digested with collagenase (see above) and revealed a ductal network similar to that observed in a prostate removed from an animal (P1, FIGS. 7B-7C). To determine if the sub-renal capsule grafts maintained a proximal-distal axis and to ascertain if cells within the proximal and distal regions of these grafts exhibited the differential growth capacity of proximal and distal cells isolated from a "primary" prostate (FIG. 7A), the recombinant tissue arising from proximal cells was dissected into proximal and distal regions. Single cell suspensions of these regions were prepared (see above) and proximal and distal cells ($1\times10^5$) were combined with UGM ($2.5\times10^5$ cells) and implanted into a second generation of recipient animals to produce a "second passage (P2)" graft (FIG. 7A). The proximal region of this P2 graft was again dissected into proximal and distal regions and the proximal region passaged as above into a third generation of recipient animals (P3, FIG. 7A). This protocol was repeated until no tissue growth was observed (FIG. 7A). After each tissue passage animals were sacrificed after 8 weeks of in vivo growth and grafts were removed and weighed.

This indicates that the sub-renal capsule tissue contains an arborizing network of ducts with a proximal-distal axis remarkably similar to that noted in a primary prostate gland. Isolated cells from the proximal regions of sequential grafts could be passaged four times before senescence, providing strong evidence for the proximal location of stem cells, not only in primary prostate tissue but also in the proximal regions of sub-renal capsule grafts. Cells isolated from the distal regions of ducts in the sub-renal capsule grafts had only a limited growth potential as was noted for cells obtained from the distal regions of ducts of primary prostate tissue. Thus cells isolated from the proximal region of grafts are able to reconstitute a structure in which cells of differing growth potential are organized along a proximal-distal axis for four successive passages.

EXAMPLE 4

Cells in the Proximal Region of Murine Prostatic Ducts Co-Express High Levels of Sca-1, Alpha 6 Integrin and Bcl-2

Figure 9:
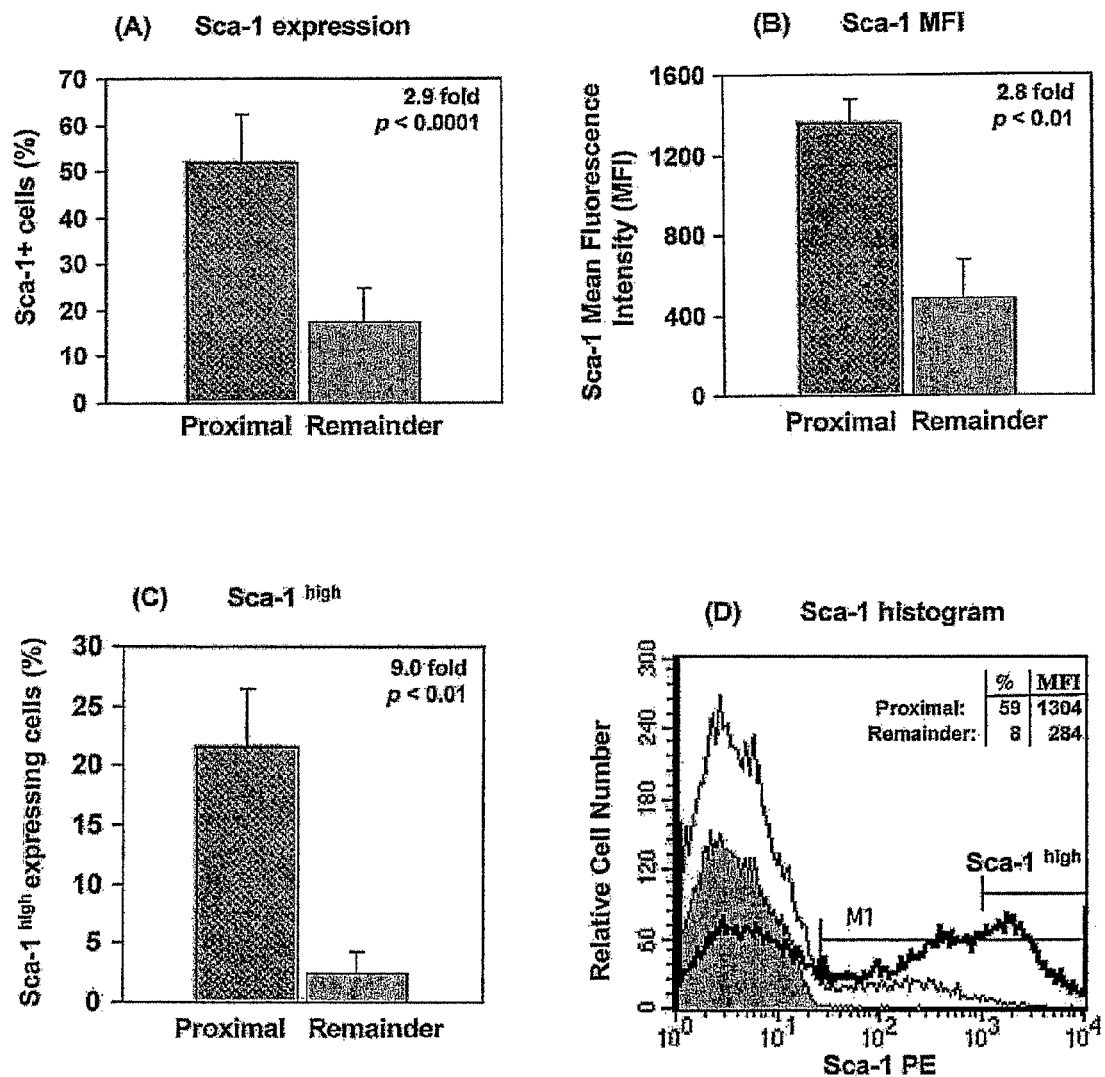
FIGS. 9A-9D show that Sca-1 is highly expressed by cells in the proximal region of prostatic ducts.

Using fluorescence activated cell sorter (FACS) analysis, it was found that Sca-1, alpha 6 integrin and Bcl-2 are expressed by at least some cells in all regions of the ducts, but significant differences were noted in their distribution. These antigens were expressed by more cells in the proximal region than in the remaining regions, and more of each antigen (increased mean fluorescence intensity, or MFI), was expressed by proximal cells than by cells in the remaining ductal regions. The proximal region contained 2.9 fold more ($p<0.0001$) Sca-1 expressing cells with higher MFI (2.8 fold, $p<0.01$) than were found in the remaining ductal regions (FIGS. 9A-9B, Tables I, II). As high levels of Sca-1 are found on purified populations of other types of stem cells (Asakura, 2003; Falciatori et al, 2004; Goodell et al, 1996; Gussoni et al, 1999), the location of cells with high MFI for Sca-1 was determined. The proximal region of ducts contained 9 fold more cells with high levels of Sca-1 (MFI >1000; Sca-1$^{high}$) than the remaining regions (Table I, $p<0.01$; FIGS. 9C-9D), indicating that Sca-1$^{high}$ cells are concentrated proximally.

Figure 8:
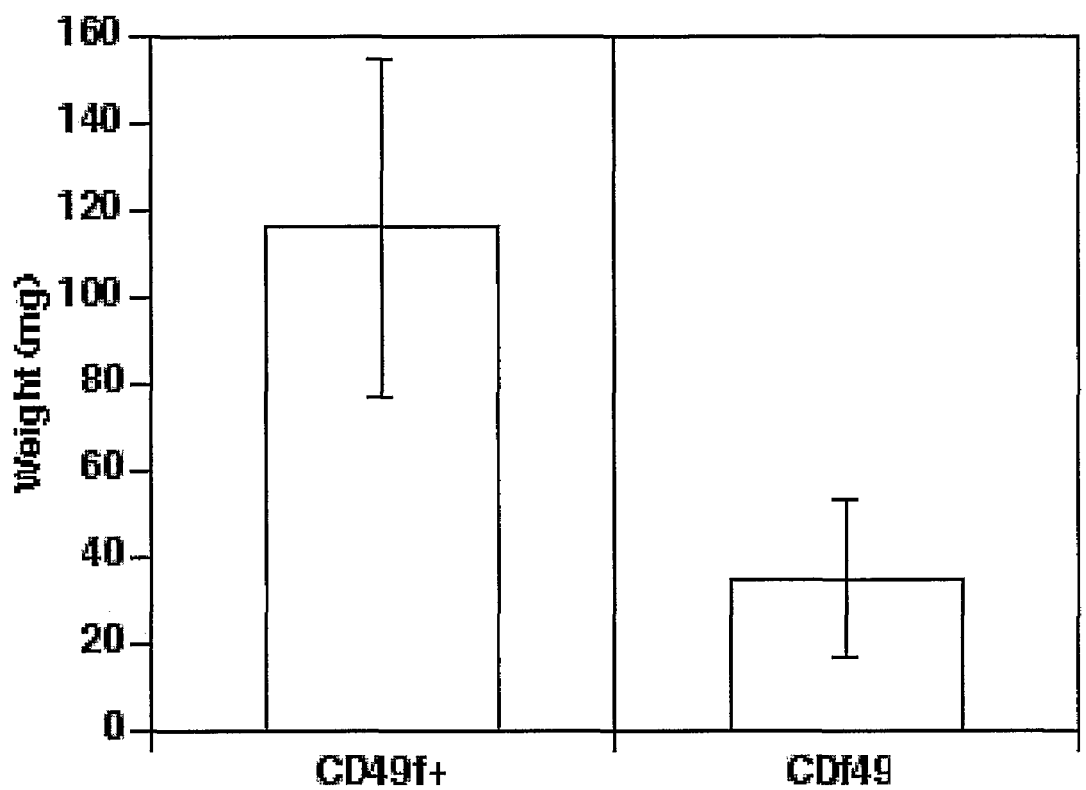
FIG. 8 indicates that alpha 6 integrin (CD49f) expressing cells isolated from the proximal region of ducts form more prostatic tissue under the renal capsule than those not expressing this integrin. Alpha 6 integrin positive and alpha 6 integrin negative cells ($10^5$) were combined with UGM cells (2.5× $10^5$) and implanted under the renal capsule. Grafts were harvested after eight weeks and weighed.
Figure 10:
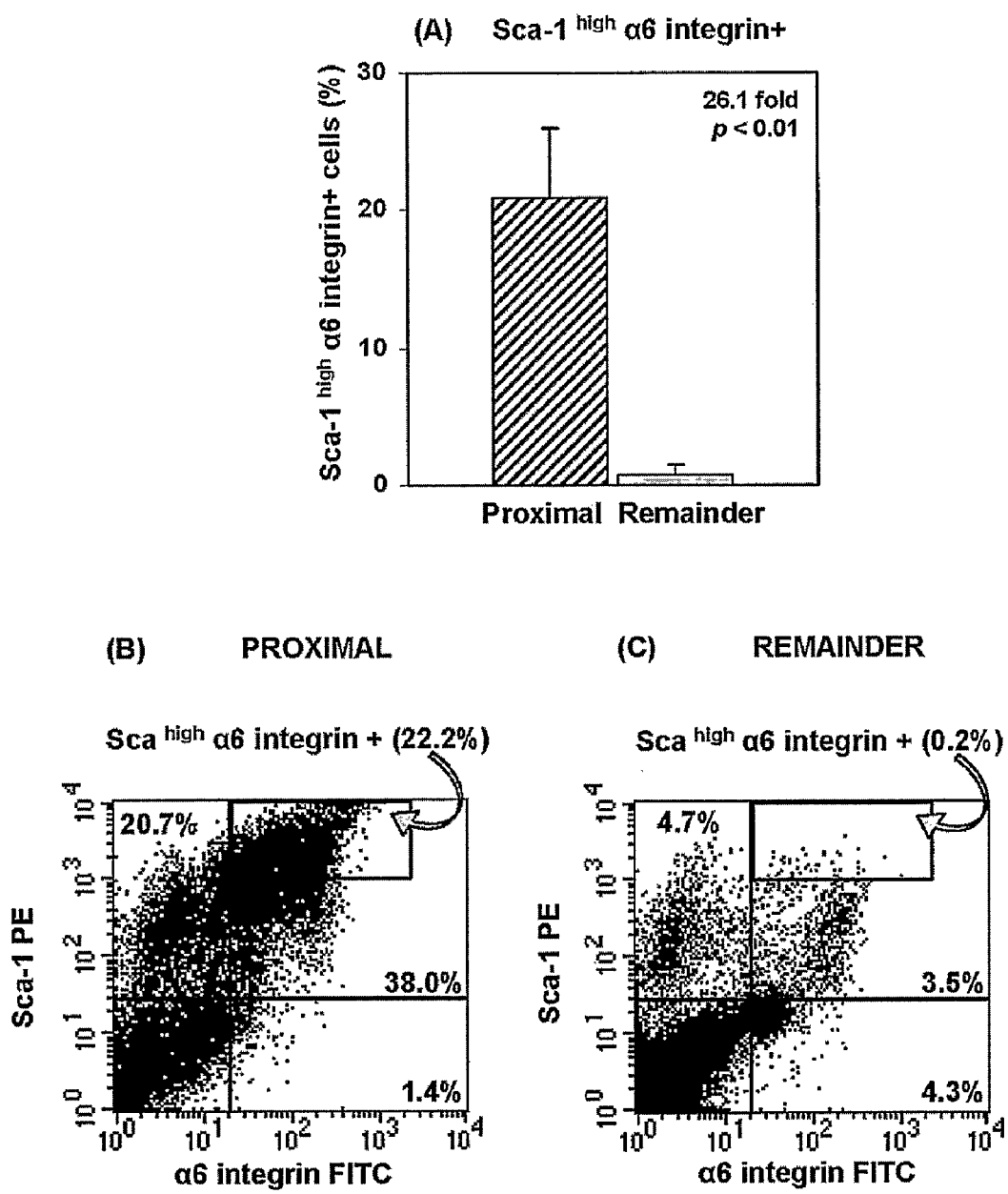
FIGS. 10A-10C show that the proximal region is enriched in Sca-$1^{high}$ alpha 6 integrin expressing cells. The expression of high levels of Sca-1 using anti-Sca-1-PE antibodies together with alpha 6 integrin was measured on cell digests from the proximal and remaining regions of prostatic ducts.
Figure 11:
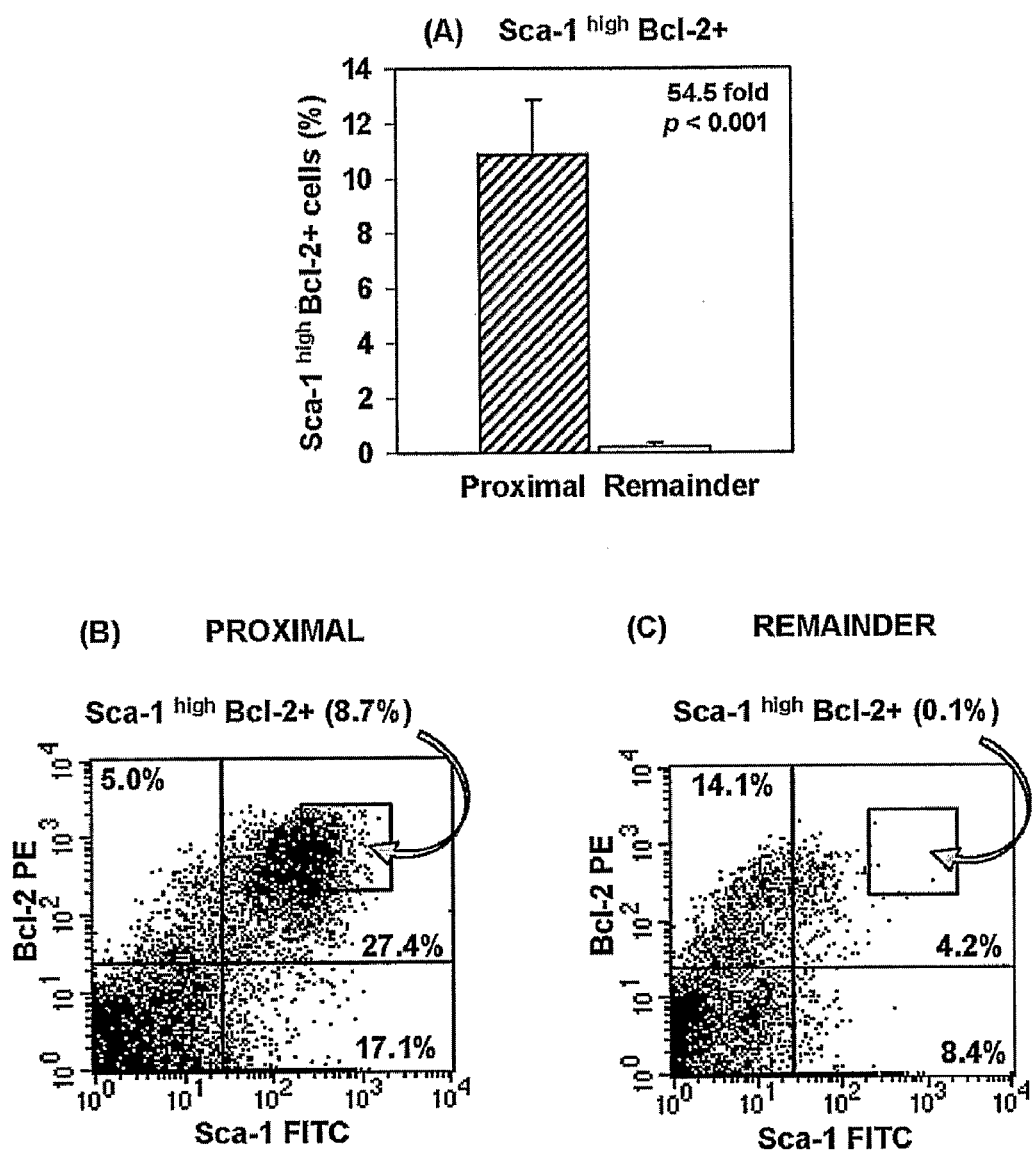
FIG. 11 shows that the proximal region is enriched in Sca-$1^{high}$/Bcl-$2^+$ cells. The expression of high levels of Sca-1 using anti-Sca-1 FITC antibodies together with Bcl-2 was determined on cell digests from the proximal and remaining regions of prostatic ducts.

The proximal region also contains more cells that express alpha 6 integrin (1.9 fold, $p<0.0001$) and Bcl-2 (1.5 fold, $p<0.0001$) with higher MFIs than the remaining ductal regions (Tables I, II). Striking differences in the distribution of cells were noted when comparing those cells expressing high levels of Sca-1 together with alpha 6 integrin or Bcl-2. The proximal region contained 26.1 fold more Sca-1$^{high}$ alpha 6 integrin co-expressing cells than the remaining ductal regions (FIG. 10A), and this cell population was almost exclusively confined to the proximal region (FIGS. 10B-10C). Similar significant differences were noted in the distribution of cells expressing high levels of Sca-1 and Bcl-2. The proximal region contained 54.5 fold more Sca-1$^{high}$ Bcl-2 expressing cells than the remaining ductal regions (FIG. 11A). Whereas a distinct Sca-1$^{high}$ Bcl-2 positive population could be seen among the cells isolated from the proximal ducts, this population was almost completely absent in cells located in the remaining regions of the ducts (FIGS. 11B-11C, 8% vs. 0.1%).

Figure 12:
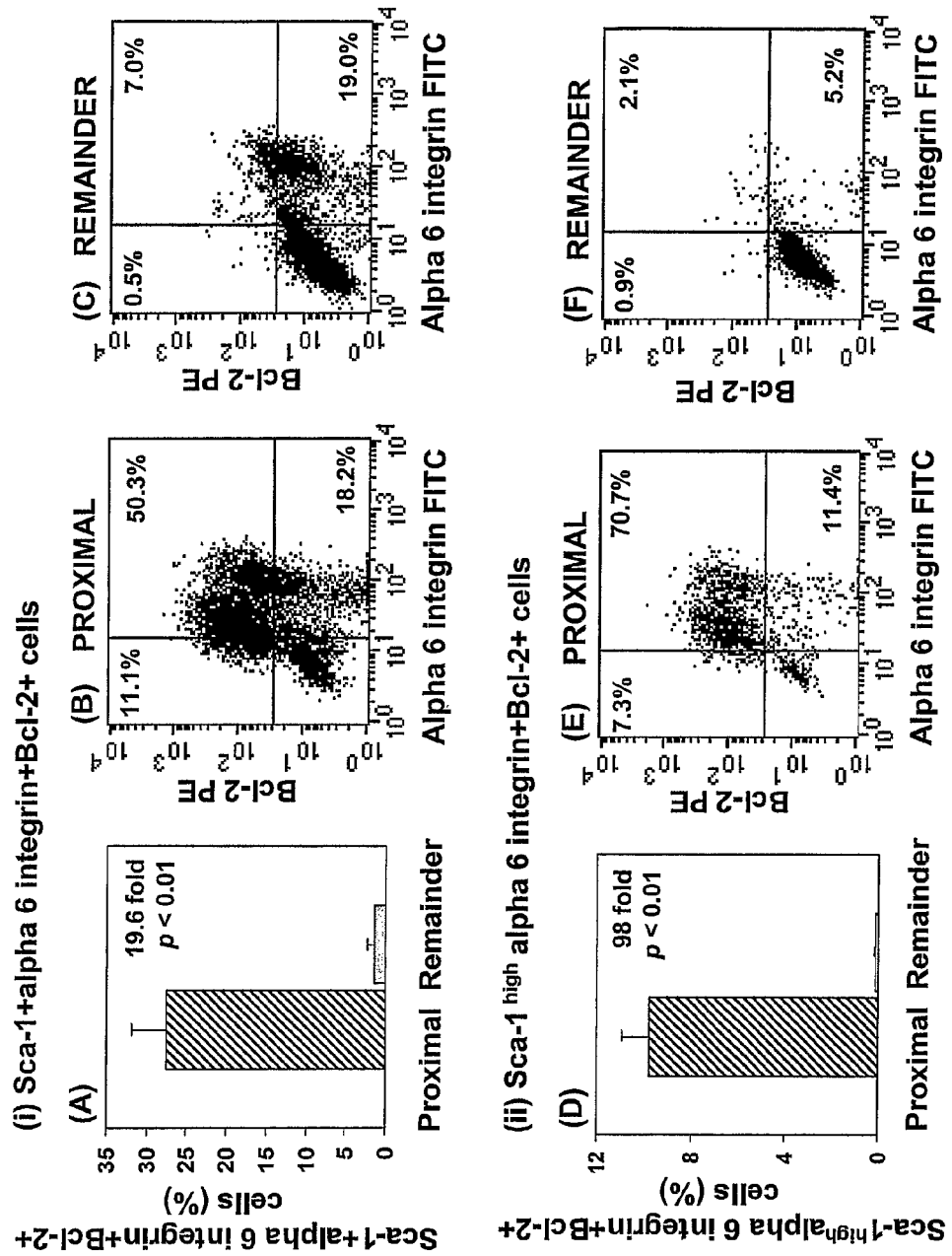
FIG. 12 shows that the proximal region is considerably enriched in Sca-1 expressing cells that co-express alpha 6 integrin and Bcl-2. Three color FACS analysis was performed to determine the incidence of (i) Sca-$1^+$/alpha 6 integrin$^+$/Bcl-$2^+$ cells and (ii) Sca-$1^{high}$/alpha 6 integrin$^+$/Bcl-$2^+$ cells in the proximal and remaining regions of ducts.

Determination of the co-expression of all three antigens (FIG. 12) indicated that cells from the proximal region contains significantly more (19.6 fold; $p<0.01$) Sca-1$^+$/alpha 6 integrin$^+$/Bcl-2$^+$ cells (27.5±4.4%) than those from the remaining regions (1.4±0.8%, FIG. 12A, Table I). Analysis of the proximal region for cells expressing high levels of Sca-1 together with α6 integrin and Bcl-2 (Sca-1$^{high}$/α6 integrin$^+$/Bcl-2$^+$ cells) revealed that 98 fold more triple labeled cells reside in the proximal compared with the other regions of ducts (9.8±1.2% versus 0.1±0.06%, $p<0.01$; FIG. 12D, Table I). In addition each antigen alone was expressed by more cells (Table 1) and with a higher MFI (Table II) in the proximal region compared with remaining regions.

These results show that there are striking differences in the distribution of cells expressing Sca-1, alpha 6 integrin, and Bcl-2 in different ductal regions. Cells with high levels of Sca-1 are predominantly confined to the proximal region and triple labeled cells with high levels of Sca-1 are almost exclusively confined to this region.

Figure 16:
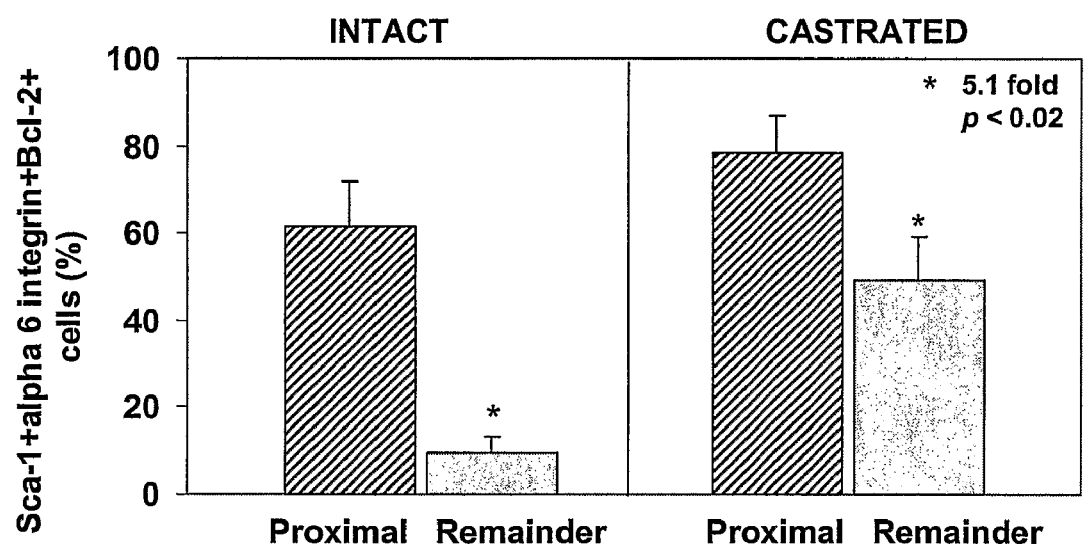
FIG. 16 shows that the expression of Sca-1$^+$/alpha 6 integrin$^+$/Bcl-2$^+$ cells increases in the remaining regions of ducts after castration. These triple-labeled cells increase 5.1 fold in the remaining ductal regions (intermediate and distal regions) after castration.
Figure 17:
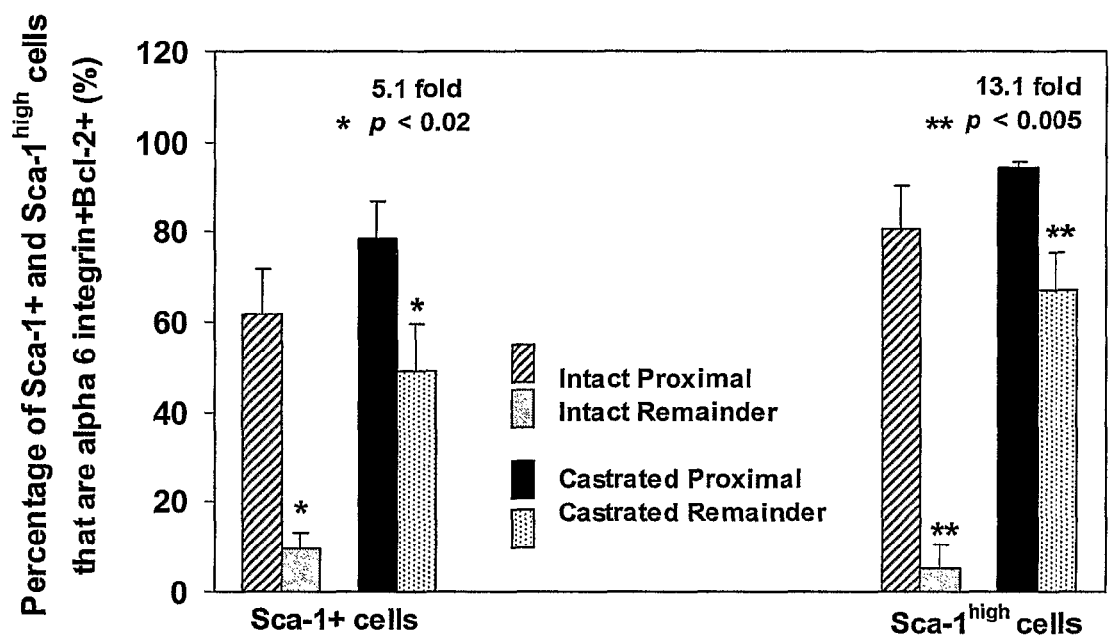
FIG. 17 shows that the expression of Sca-1$^+$ and Sca-1$^{high}$ cells that co-express alpha 6 integrin and Bcl-2 is increased in the remaining (intermediate and distal regions) regions of ducts after castration. Castration resulted in a 5.1 fold increase in Sca-1$^+$/alpha 6 integrin$^+$/Bcl-2$^+$ cells in the remaining ductal regions, and a 13.1 fold increase in Sca-1$^{high}$/alpha 6 integrin$^+$/Bcl-2$^+$ in the remaining ductal regions.

FIGS. 16 and 17 support the findings that primitive (stem) cells have the phenotype Sca-1$^+$/alpha 6 integrin$^+$/Bcl-2$^+$, and that most primitive cells with this phenotype express high levels of Sca-1. Castration results in the involution of the prostate and many cells are lost due to apoptosis. The prostate should therefore be enriched, after castration, for cells with a primitive phenotype.

FIGS. 16 and 17 show that the percentages of cells in the proximal region that are triple labeled do not change much after castration. However, the percentages of cells in the remaining regions of ducts that are triple labeled are considerably enriched after castration. Many mature cells will die during involution. Thus, one would expect an enrichment of immature cells in these regions after castration. The present inventors have demonstrated that after castration triple labeled cells with high levels of Sca-1 increase 13.1 fold (FIG. 17) in the remaining regions (intermediate and distal) of ducts, indicating that this is a primitive cell phenotype.

Figure 18:
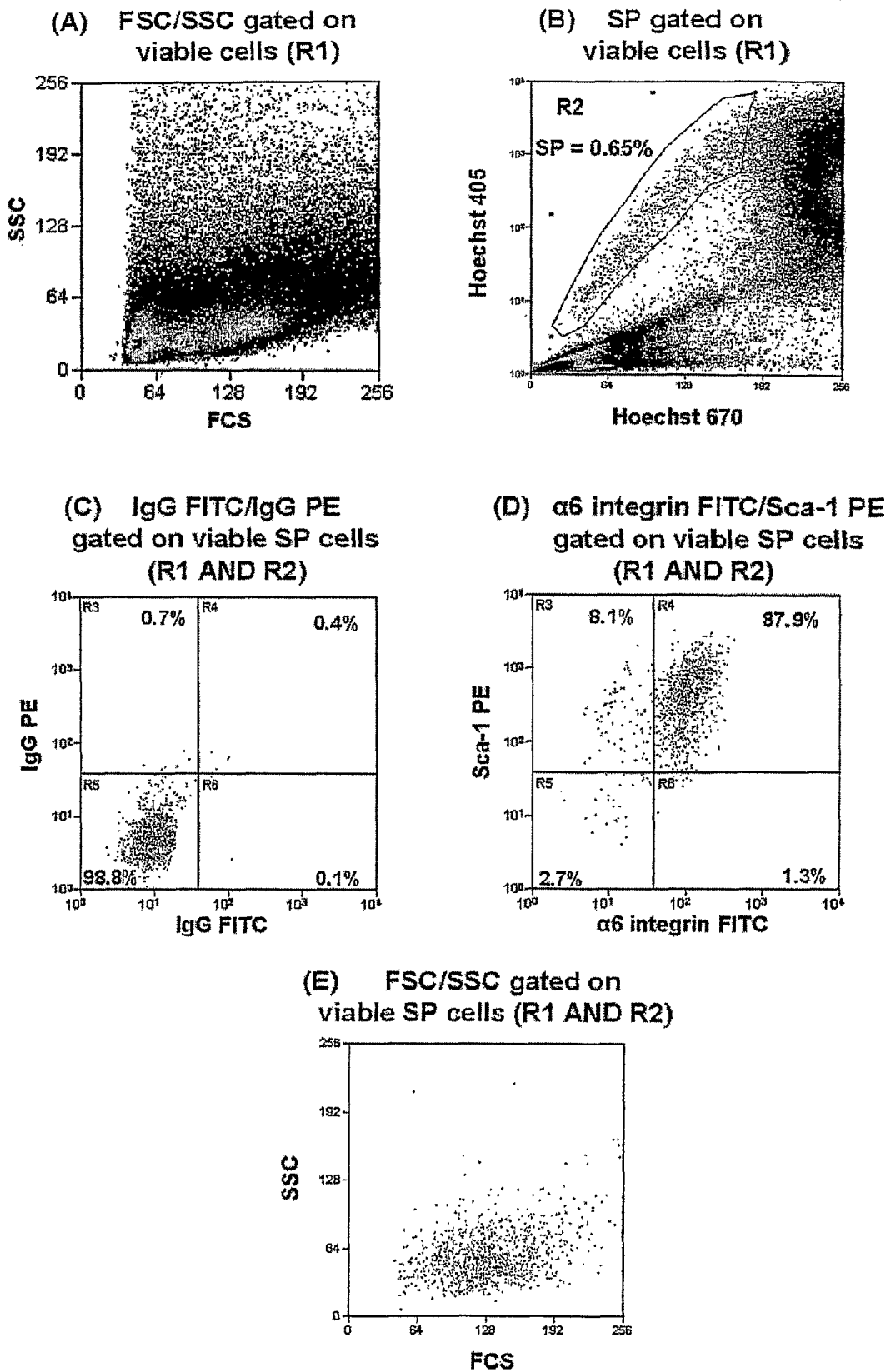
FIG. 18 shows that the prostate contains side population (SP) cells that express Sca-1 and alpha 6 integrin. Side population cells, that have been shown in other organs to have stem cell characteristics, are found in the prostate and 88% express Sca-1 and alpha 6 integrin.

Stem cells from a variety of tissues including bone marrow, skeletal and cardiac muscle, breast, brain, liver, kidney, lung and small intestine (Uchida et al, 2001; Goodell, 2000; Goodell et al, 1996; Goodell et al, 1997; Asakura et al, 2002a; Asakura et al, 2002b; Hierlihy et al, 2002; Welm et al, 2002; Murayama et al, 2002; Alvi et al, 2002) actively efflux the Hoechst dye 33342 through the activity of multi-drug resistance (MDR)-like proteins (Zhou et al, 2001; Scharenburg et al, 2002; Zhou et al, 2002), and this property has been used to characterize and isolate them as a side population (SP). FIG. 18 shows that a side population of cells are present in the prostate and that most of these cells (88%) express Sca-1 and alpha 6 integrin (FIG. 18D).

This SP technique has the considerable advantage that cells with primitive features can be isolated in the absence of known stem cell markers. As almost all side population cells in the prostate express Sca-1 and alpha 6 integrin this indicates that these antigens must be present on prostate stem cells.

TABLE I

Expression of Sca-1, α6 Integrin and Bcl-2 by Cells from the Proximal Region of Prostatic Ducts Compared with cells from the Remaining Ductal Regions

| Phenotype | Experiments (n) | Proximal Expression (%) | Remainder Expression (%) | Increase (fold) | p value |
|---|---|---|---|---|---|
| Sca-1$^+$ | 16 | 51.8 ± 10.5 | 17.7 ± 7.2 | 2.9 | <0.0001 |
| α6 integrin$^+$ | 13 | 40.8 ± 10.0 | 21.1 ± 11.4 | 1.9 | <0.0001 |
| Bcl-2$^+$ | 12 | 42.1 ± 7.0 | 27.5 ± 8.2 | 1.5 | <0.0001 |
| Sca-1$^+$/α6integrin$^+$ | 4 | 37.7 ± 11.6 | 9.0 ± 5.8 | 4.2 | <0.01 |
| Sca-1$^+$/Bcl-2$^+$ | 5 | 28.3 ± 1.9 | 5.3 ± 1.9 | 5.3 | <0.0001 |
| Sca-1$^+$/α6integrin$^+$/Bcl-2$^+$ | 3 | 27.5 ± 4.4 | 1.4 ± 0.8 | 19.6 | <0.01 |
| Sca-1$^{high}$(PE)$^{(a)}$ | 4 | 21.6 ± 4.9 | 2.4 ± 1.9 | 9.0 | <0.01 |
| Sca$^{high}$(PE)$^{(a)}$/α6 integrin$^+$(FITC) | 4 | 20.9 ± 5.1 | 0.8 ± 0.7 | 26.1 | <0.01 |

TABLE I-continued

Expression of Sca-1, α6 Integrin and Bcl-2 by Cells from the
Proximal Region of Prostatic Ducts Compared with cells from the
Remaining Ductal Regions

| Phenotype | Experiments (n) | Proximal Expression (%) | Remainder Expression (%) | Increase (fold) | p value |
|---|---|---|---|---|---|
| Sca-1$^{high}$(FITC)[b] | 5 | 13.6 ± 2.5 | 1.5 ± 0.4 | 9.1 | <0.001 |
| Sca$^{high}$(FITC)[b]Bcl-2$^+$(PE) | 5 | 10.9 ± 2.0 | 0.2 ± 0.2 | 54.5 | <0.001 |
| Sca$^{high}$(APC)[c]/α6integrin$^+$(FITC)/Bcl-2$^+$(PE) | 3 | 9.8 ± 1.2 | 0.1 ± 0.06 | 98.0 | <0.01 | n = number of experiments
[a]Sca-1$^{high}$ = cells with MFI > 1000 for anti-Sca-1 PE
[b]Sca-1$^{high}$ = cells with MFI > 200 for anti-Sca-1 FITC
[c]Sca-1$^{high}$ = cells with MFI > 200 for anti-Sca-1 biotin plus streptavidin APC As PE has a higher intensity than FITC, cells with MEI >1000 for anti-Sca-1 PE or >200 for anti-Sca-1 FITC or streptavidin APC were considered to express high levels of Sca-1 (Sca-1$^{high}$).

TABLE II

Mean fluorescence intensity (MFI) of antigens expressed by cells from the proximal region of prostatic ducts compared with cells from the remaining ductal regions.

| | Experiments (n) | Fluorochrome[a] | Proximal MFI | Remainder MFI | Increase (fold) | p value |
|---|---|---|---|---|---|---|
| Sca-1$^+$ | 5 | PE(Sca-1) | 1356 ± 124 | 483 ± 194 | 2.8 | <0.01 |
| α6 integrin$^+$ | 5 | FITC(α6 integrin) | 123 ± 13 | 88 ± 8 | 1.4 | <0.001 |
| Bcl-2$^+$ | 12 | PE(Bcl-2) | 450 ± 104 | 203 ± 96 | 2.2 | <0.0001 |
| Sca-1$^+$α6integrin$^+$ | 4 | PE(Sca-1) | 1839 ± 321 | 320 ± 67 | 5.7 | <0.01 |
| Sca-1$^+$α6integrin$^+$ | 4 | FITC(α6 integrin) | 126 ± 12 | 117 ± 9 | 1.1 | NS |
| Sca-1$^+$Bcl-2$^+$ | 5 | FITC(Sca-1) | 209 ± 31 | 89 ± 53 | 2.3 | <0.02 |
| Sca-1$^+$Bcl-2$^+$ | 5 | PE(Bcl-2) | 529 ± 161 | 381 ± 122 | 1.4 | <0.01 | n = number of experiments
NS = not significant
[a]Fluorochrome conjugated antibodies used: anti-Sca-1 PE, anti-Sca-1 FITC, anti-α6 integrin FITC, anti-Bcl-2 PE. The MFI values for PE conjugated antibodies are higher than those for FITC conjugated antibodies as PE has a greater fluorescence intensity than FITC.

EXAMPLE 5

Sca-1 and Alpha 6 Integrin Expressing Cells Have High In Vivo Proliferative Potential The ability to regenerate tissue in vivo is a characteristic of stem cells, and this property has been used to identify various antigens, including Sca-1, as stem cells markers. For example, Sca-1 expressing cells isolated from bone marrow are able to reconstitute all blood cell types (Spangrude et al, 1988), and mammary epithelial cells enriched for Sca-1 can reconstitute the mammary gland in vivo and have greater growth potential than Sca-1 depleted cells (Welm et al, 2002).

Figure 13:
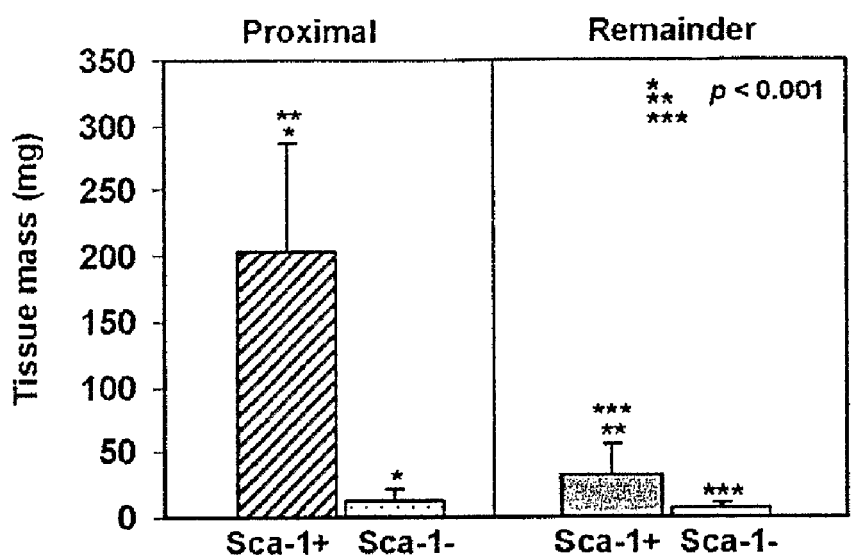
FIG. 13A shows the growth of Sca-$1^+$ cells and Sca-$1^-$ cells ($10^5$ cells) that were isolated from either the proximal or the remaining regions of prostatic ducts and transplanted under the renal capsule and measured after eight weeks. Sca-$1^+$ cells, obtained from the remaining ductal regions, had far less growth potential than Sca-$1^+$ proximal cells.
FIG. 13B shows prostate tissue under the renal capsule initiated with $10^5$ Sca-$1^+$ or Sca-$1^-$ cells from either the proximal or remaining ductal regions.
Figure 13:
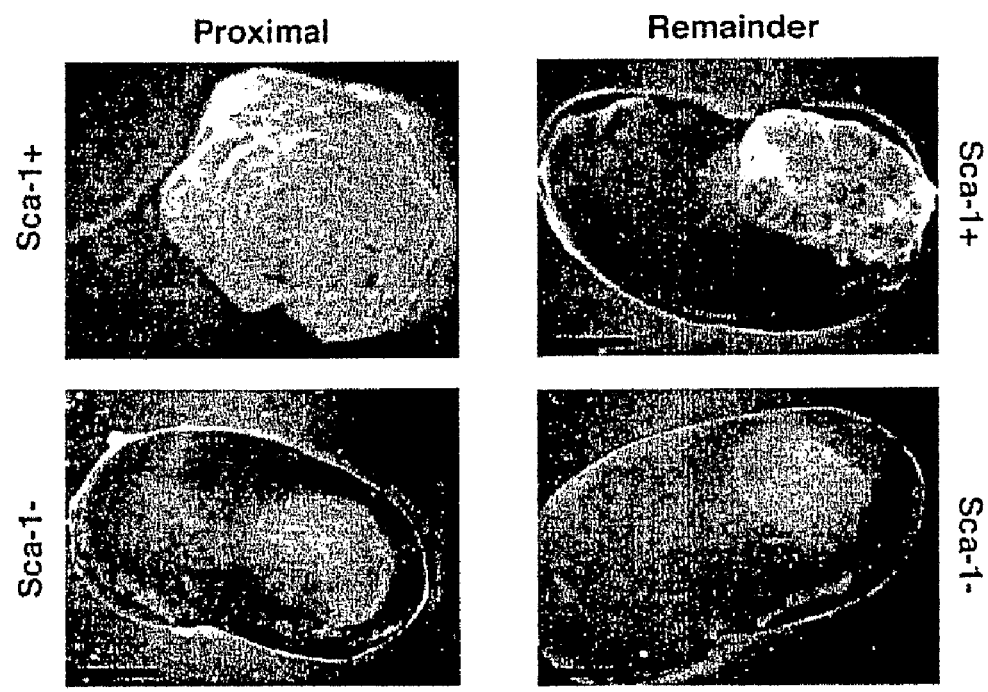
Figure 14:
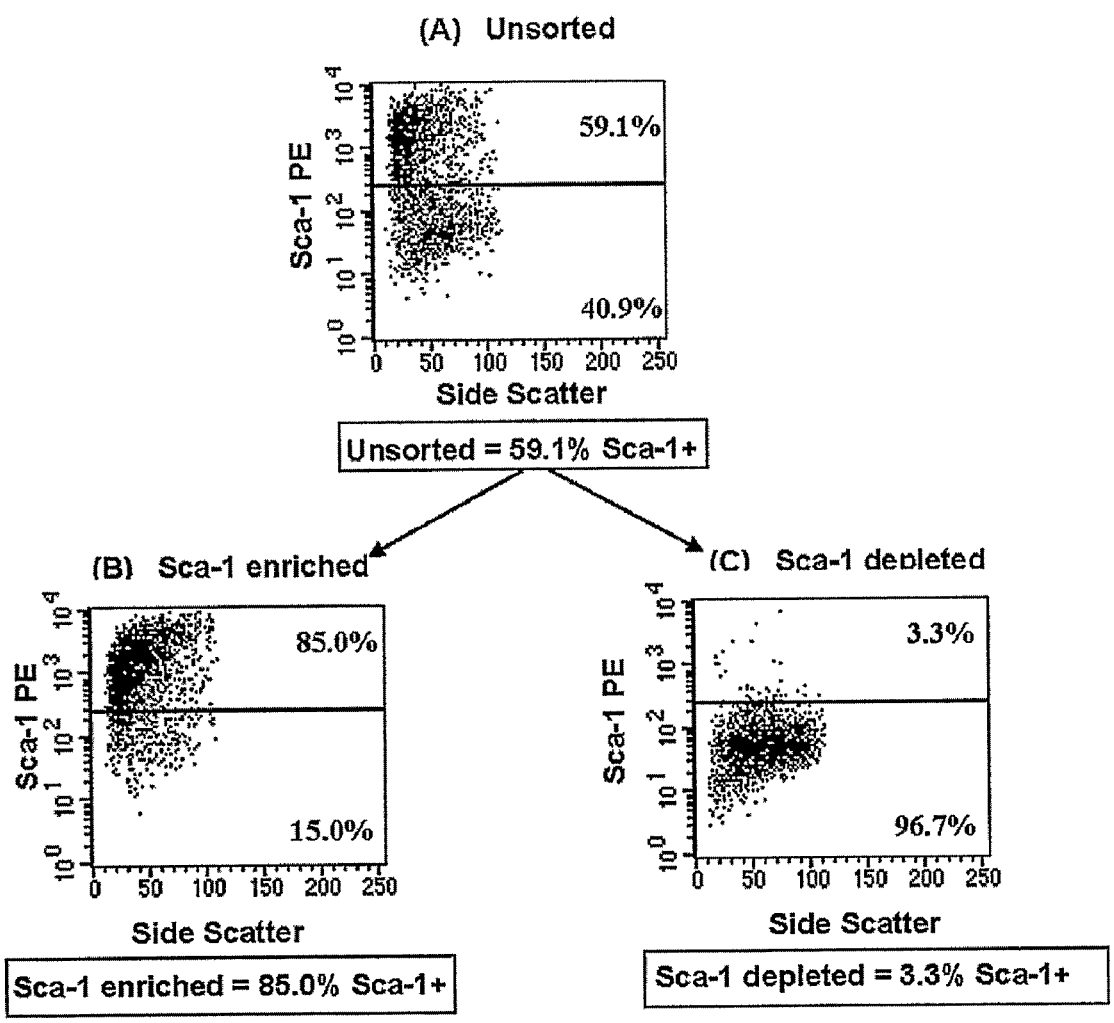
FIGS. 14A-14C depict immunomagnetic separation of Sca-1 enriched and Sca-1 depleted populations. FACS analysis of Sca-1 enriched and Sca-1 depleted cells isolated from the proximal region of prostatic ducts using magnetic beads coated with antibodies to Sca-1 showed that this technique resulted in good separation of Sca-1 positive from Sca-1 negative cells.

The growth potential of Sca-1 expressing cells isolated from the proximal and the remaining ductal regions was determined, and their proliferative potential in vivo was compared with cells that did not express this antigen. Sca-1 expressing (Sca-1$^+$) and Sca-1 depleted (Sca-1−) populations were isolated from digests of the proximal and the remaining ductal regions using antibodies to Sca-1 and magnetic microbeads. These populations were combined with cells isolated from the urogenital sinus mesenchyme (inductive mesenchyme for prostatic tissue, Cunha et al, 1987b; Norman et al, 1986; Xin et al, 2003), inserted under the renal capsule of recipient male animals and the amount of prostatic tissue generated was measured after eight weeks. Sca-1 expressing cells isolated from the proximal region formed significantly more prostatic tissue (203.0±83.1 mg, 17.1 fold) than was obtained from the Sca-1 depleted proximal population (11.9±9.2 mg; p<0.001, FIGS. 13A and 13B). Sca-1 expressing cells isolated from the remaining ductal regions also formed prostatic tissue under the renal capsule (31.0±24.1 mg) but formed far less tissue than observed for Sca-1 expressing cells isolated from the proximal region (203.0±83.1 mg), indicating that these two Sca-1 expressing populations differ markedly in their in vivo growth potential (p<0.001). Sca-1 depleted cells isolated from the remaining regions of ducts formed very little sub-renal capsule tissue (6.6±5.0 mg). FACS analysis of cells isolated using magnetic beads showed that whereas 59.1% of unsorted cells obtained from the proximal regions expressed Sca-1, as shown in FIG. 14A, 85.0% of the Sca-1 enriched sample expressed this antigen, as shown in FIG. 14B. Only 3.3% of the cells from the Sca-1-depleted sample expressed Sca-1 (FIG. 14C), indicating that this technique resulted in good separation of Sca-1 positive from Sca-1 negative cells.

As the FACS data showed that cells expressing high levels of Sca-1 were confined predominantly to the proximal region of ducts, it was determined whether Sca-1$^{high}$ cells had a greater growth potential than cells with medium/low Sca-1 expression. Proximal cell digests were FACS sorted into fractions containing cells with high MFI (Sca-1$^{high}$), medium to low MFI (Sca-1$^{med/low}$) and no Sca-1 expression (Sca-1$^{negative}$) and inserted under the renal capsule of recipient animals.

Figure 15:
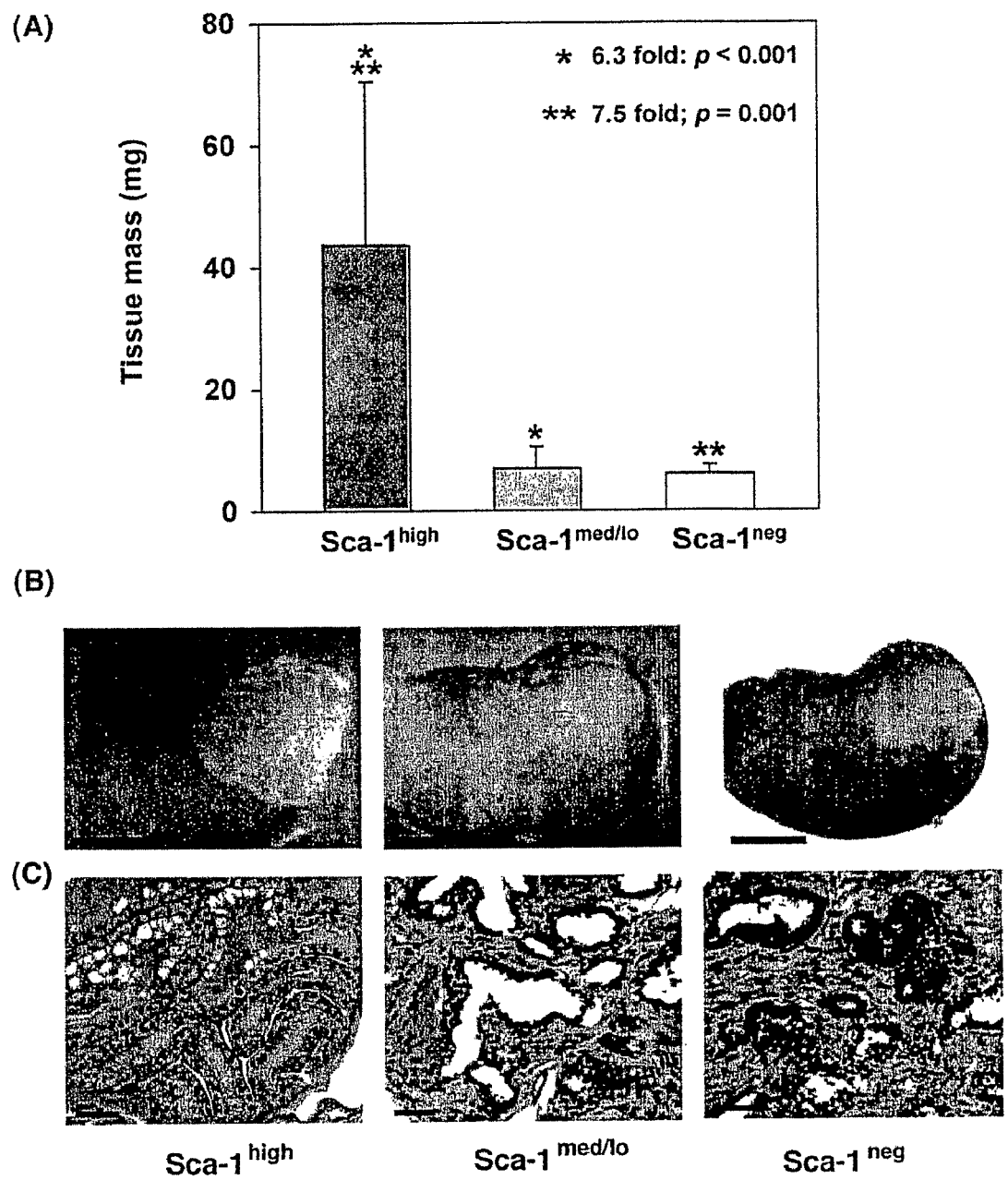
FIGS. 15A-15C show that Sca-$1^{high}$ cells have greater in vivo proliferative capacity than cells that express lower levels of Sca-1. Cells were isolated from the proximal region of prostatic ducts and sorted by FACS into Sca-$1^{high}$, Sca-$1^{med/low}$, and Sca-$1^{negative}$ fractions according to the level of Sca-1 expression. The cell populations were transplanted under the renal capsule, and the growth of prostatic tissue obtained from the various fractions was measured after ten weeks.

Sca-1$^{high}$ cells formed significantly more prostatic tissue (43.7±26.8 mg; 6.3 fold) than Sca-1$^{med/low}$ cells (6.9±3.6 mg; p<0.001) and 7.5 fold more tissue than Sca-1$^{negative}$ cells (5.8±1.6 mg; p=0.001, FIGS. 15A-15C). Although the tissue growth obtained was less than in experiments using magnetic beads (due to the stress that the cells undergo during FACS sorting), these results show that almost all of the in vivo growth potential is confined to cells that express high levels of Sca-1. The prostatic tissue obtained from Sca-1$^{high}$ cells had normal prostatic histology, comprising basal and luminal cells lining prostatic ducts. The lumens of the ducts contain abundant amounts of secretory material (FIG. 15C). In contrast, the tissue arising from Sca-1$^{med/low}$ cells and Sca-1$^{negative}$ cells contained far more stroma with less of an epithelial component, and not much secretory material was noted within the ducts FIG. 15C.

These results show that cells expressing Sca-1 have considerably more growth potential than those lacking this antigen, and that the proliferative ability within the Sca-1 expressing proximal cells resides in cells that express high levels of this antigen. They also show that Sca-1 expressing cells residing in the proximal region are more primitive than those Sca-1 expressing cells in the remaining ductal regions, as they have far higher proliferative capacity. These data indicate that stem cells reside within the Sca-1 expressing population in the proximal region, whereas the transit-amplifying cells, with more limited growth potential, reside within the Sca-1 expressing cells in the remaining ductal regions.

Sca-1 is expressed by stem cells from a variety of origins including hematopoietic tissue, heart, mammary gland, skin, muscle and testis (Asakura, 2003; Falciatori et al, 2004; Matsuura et al, 2004; Montanaro et al, 2003; Spangrude et al, 1988; Welm et al, 2002). Although the ligand for Sca-1 has not been identified, it is important for the self-renewal of mesenchymal (Bonyadi et al, 2003) and hematopoietic (Ito et al, 2003) stem cells. Sca-1$^{-/-}$ mice have greatly reduced bone mass resulting from a primary defect in the self-renewal capacity of early mesenchymal progenitor cells (Bonyadi et al, 2003). In addition, hematopoietic stem cells from Sca-1$^{-/-}$ mice have decreased repopulation potential and lower engraftment of secondary transplants than wild type mice (Ito et al, 2003), indicating that Sca-1 is required for self-renewal. These findings are consistent with our data showing little in vivo growth of prostatic tissue under the renal capsule from Sca-1 negative cells, and indicate that Sca-1 may also be involved in the self-renewal of prostatic stem cells.

Significantly more Sca-1$^{high}$ alpha 6 integrin positive cells are found in the proximal region compared with the remaining regions of the ducts. Alpha 6 integrin and high levels of Sca-1 are also expressed on spermatogonial stem cells (Falciatori et al, 2004). Stem cells from other origins also express alpha 6 integrin. The gene for this antigen was the only common gene identified in a study using transcriptional profiling to identify genes expressed by stem cells of embryonic, neural, hematopoietic and retinal origin (Fortunel et al, 2003). Keratinocyte stem cells also express high levels of alpha 6 integrin (Li et al, 1998) and these cells have enhanced long term proliferative potential (Kaur et al, 2000).

As alpha 6 integrin is expressed by a variety of stem cells (Falciatori et al, 2004; Fortunel et al, 2003; Li et al, 1998; Kaur et al, 2000), cells expressing this antigen were isolated from the proximal region of the prostate using magnetic microbeads and antibodies to alpha 6 integrin. The present inventors found that alpha 6 integrin expressing cells formed more prostatic tissue (116.3±38.9 mg) under the renal capsule than cells that lacked alpha 6 integrin expression (34.9±18.1 mg) (p=0.02) (FIG. 8). This data indicates that proximal stem cells lie within the population that expresses alpha 6 integrin as these cells have greater in vivo proliferative activity than cells lacking expression of this antigen.

Members of the integrin family are important regulators of stem cell function (Watt, 2002). Keratinocyte and prostatic stem cells are more adhesive than the more mature transit-amplifying cells (Bickenbach et al, 1998; Collins et al, 2001; Jones et al, 1993) and antibodies to alpha 6 integrin inhibit the adhesion and migration of hematopoietic stem cells (Gu et al, 2003). In addition, there is recent evidence that the adhesive properties of integrins may be involved in maintaining stem cells within their niche (Campos et al, 2004; Fuchs et al, 2004). Since stem cells and cancer cells have many similar properties (Al-Hajj et al, 2004; Al-Hajj et al, 2003; Lapidot et al, 1994; Pardal et al, 2003; Reya et al, 2001), it is of interest that changes in the expression of integrins, particularly alpha6β4 integrin, are implicated in tumorigenesis and invasion and that the alpha 6 integrins play a role in the progression of breast (Chung et al, 2004), colorectal (Chao et al, 1996) and prostate cancer (Cress et al, 1995). The use of integrins and inhibitory antibodies to these proteins is currently being investigated as possible strategies for developing novel anti-cancer therapies (Rust et al, 2002; Slack-Davis et al, 2004).

There is additional evidence for the proximal location of prostatic stem cells. This region is least affected by castration in terms of apoptosis and cell loss (Lee et al, 1990; Rouleau et al, 1990) and has the highest levels of telomerase (Banerjee et al, 1998a) that is associated with germinative compartments of many self-renewing tissues (Caporaso et al, 2003). Cells in the proximal region also respond differentially to those in the distal region after androgen manipulation as far as TGF-alpha expression is concerned (Banerjee et al, 1998b). The levels of TGF-alpha in the distal regions are negligible in distal cells of intact animals while being prominent in proximal cells. After castration expression in proximal cells is unchanged, whereas the expression in distal cells is markedly increased, leading to the hypothesis that TGF-alpha may be a survival factor for the proximal epithelial cells, protecting them from apoptotic death after androgen ablation. Stem cells are thought to reside in 'niches' in microenvironments that protect and nurture them (Lemischka et al, 2003). As cells in the proximal region are resistant to the effects of castration and as the present inventors show that isolated cells from the proximal region survive androgen deprivation it is likely that the proximal region of prostatic ducts contains a niche for these stem cells.

It is of interest that the tissue arising from proximal cells after prolonged androgen deprivation followed by androgen administration contains significantly more smooth muscle than the tissue formed in the continuous presence of androgens. The reason for this is unknown but the appearance is reminiscent of that of BPH in which an increased stromal component is present (Shapiro et al, 1992). These data suggest that a period of diminished exposure to androgens followed by androgen supplementation may alter the epithelial/stromal interactions in a manner that promotes stromal cell proliferation.

EXAMPLE 6

Expression of Prominin and FGFR by Cells in the Proximal Region

As prominin (CD133) (Yin et al, 1997; Richardson et al, 2004) and FGFR-1 (Burger et al, 2002; de Haan et al, 2003) are expressed on primitive cells we determined if they were differentially expressed by prostate cells in different regions of the ducts and if they were co-expressed on Sca-1 expressing cells. The present inventors show (Table III) that prominin (CD133) and receptors for FGF (FGF-R1) are expressed by prostatic stem cells as both these proteins are expressed on Sca-1 expressing cells. Table III indicates that significantly more Sca-1 and Sca-1$^{high}$ cells express prominin and FGF-R1 in the proximal region than in remaining ductal regions indicating that prominin and FGFR expressing primitive cells are concentrated in the proximal region. It also shows that castration enriches for these triple labeled cells (Sca-1$^+$/prominin$^+$/FGFR$^+$) in the remaining regions indicating that they must be expressed on primitive cells that do not die during castration.

TABLE III

Expression of Sca-1, Prominin and FGFR by Cells from the Proximal Region of Prostatic Ducts Compared with Cells from the Remaining Ductal Regions from Intact and Castrated Mice

| Phenotype | INTACT | | CASTRATED | |
|---|---|---|---|---|
| | Proximal (%) | Remainder (%) | Proximal (%) | Remainder (%) |
| Sca-1$^+$prominin$^+$ | 13.2 | 3.6 | 11.5 | 11.3 |
| Sca-1$^+$FGFR$^+$ | 36.3 | 17.0 | 42.5 | 15.1 |
| Sca-1$^+$prominin$^+$FGFR$^+$ | 10.2 | 2.0 | 8.9 | 4.5 |
| Sca-1$^{high}$prominin$^+$FGFR$^+$ | 6.9 | 0.1 | 4.7 | 1.2 |

EXAMPLE 7

Predominance of Frizzled Protein, CD34 and Notch on Cells in the Proximal Region There are also differences in the distribution of cells that co-express Sca-1, Frizzled 3 (Fzd3) and Notch1 protein between the different regions of the ducts. Sca-1$^+$/Fzd3$^+$ cells comprise 14.4%±6.6% of cells in the proximal region, while only 2.8±0.4% of cells from the remaining ductal regions co-express these antigens. Frizzled proteins are receptors for Wnt proteins and Wnts are implicated in the self-renewal of stem cells (Reya et al, 2005; Reya et al, 2003; Willert et al, 2003).

Furthermore, it has been found that 3.3%±0.4% of cells from the proximal region of the ducts express CD34 and more than 85% of these CD34$^+$ cells co-express alpha 6 integrin. The number of triple labeled Sca-1$^+$/alpha 6 integrin$^+$/Notch$^+$ in the proximal region is 5.4%. The number of triple labeled Sca-1$^+$/alpha 6 integrin$^+$/Notch$^+$ in the remaining regions is 0.3%. The number of double labeled alpha 6 integrin$^+$/Notch$^+$ cells in the proximal region is 10.8%. The number of double labeled alpha 6 integrin$^+$/Notch$^+$ in the remaining regions is 5.5%. The number of double labeled Sca-1$^+$/Notch$^+$ cells in the proximal region is 6.2%. The number of double labeled Sca-1$^+$/Notch$^+$ in the remaining regions is 0.4%. The number of single labeled Notch$^+$ cells in the proximal region is 14.0%. The number of single labeled Notch$^+$ cells in the remaining regions is 8.9%. Notch is another antigen found in human cells.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Adams et al, "The Bcl-2 protein family: arbiters of cell survival", Science 281:1322-1326 (1998)
Al-Hajj et al, "Self-renewal and solid tumor stem cells", Oncogene 23: 7274-7282 (2004)
Al-Hajj et al, "Prospective identification of tumorigenic breast cancer cells", Proc Natl Acad Sci USA 100(7):3983-3988 (2003)
Alvi et al, "Functional and molecular characterisation of mammary side population cells", Breast Cancer Res 5:R1-8 (2002)
Asakura A, "Stem cells in adult skeletal muscle", Trends Cardiovasc Med 13:123-128 (2003)

Asakura et al, "Side population cells from diverse adult tissues are capable of in vitro hematopoietic differentiation", *Exp Hematol* 30:1339-1345 (2002a)

Asakura et al, "Myogenic specification of side population cells in skeletal muscle", *J Cell Biol* 159:123-134 (2002b)

Banerjee et al, "Telomerase activity in normal adult Brown Norway rat seminal vesicle: regional distribution and age-dependent changes", *Endocrinology* 139(3):1075-1081 (1998a)

Banerjee et al, "Regional expression of transforming growth factor-alpha in rat ventral prostate during postnatal development, after androgen ablation, and after androgen replacement", *Endocrinology* 139(6):3005-3013 (1998b)

Berry et al "Germ-line tumor formation caused by activation of glp-1, a *Caenorhabditis elegans* member of the Notch family of receptors", *Development* 124(4):925-936 (1997)

Bickenbach et al, "Selection and extended growth of murine epidermal stem cells in culture", *Exp Cell Res* 244:184-189 (1998)

Blattler et al, "Acid-Cleavable Compound, Use in Protein Conjugates and Drug Delivery Systems", U.S. Pat. No. 4,569,789, issued Feb. 11, 1986

Bonnet et al, "Human acute myeloid leukemia is organized as a hierarchy that originates from a primitive hematopoietic cell", *Nat Med* 3(7):730-737 (1997)

Bonyadi et al, "Mesenchymal progenitor self-renewal deficiency leads to age-dependent osteoporosis in Sca-1/Ly-6A null mice", *Proc Natl Acad Sci USA* 100:5840-5845 (2003)

Bruckheimer et al, "Regulation of Bcl-2 expression by dihydrotestosterone in hormone sensitive LNCaP-FGC prostate cancer cells", *J Urol* 169:1553-1557 (2003)

Budavari et al (eds.), *Merck Index: An Encyclopedia of Chemicals, Drugs and Biologicals*, 12$^{th}$ Edition, CRC Press (1996)

Burger et al, "Fibroblast growth factor receptor-1 is expressed by endothelial progenitor cells", *Blood* 100(10):3527-3535 (2002)

Campos et al, "Beta1 integrins activate a MAPK signalling pathway in neural stem cells that contributes to their maintenance", *Development* 131:3433-3444 (2004)

Caporaso et al, "Telomerase activity in the subventricular zone of adult mice", *Mol Cell Neurosci* 23(4):693-702 (2003)

Chao et al, "A function for the integrin alpha6beta4 in the invasive properties of colorectal carcinoma cells", *Cancer Res* 56:4811-4819 (1996)

Chen et al, "Genetic regulation of primitive hematopoietic stem cell senescence", *Exp Hematol* 28(4):442-450 (2000)

Chung et al, "Contributions of the alpha6 integrins to breast carcinoma survival and progression", *Mol Cells* 17:203-9 (2004)

Civin C I, "Human Stem Cells", U.S. Pat. No. 4,714,680, issued Dec. 22, 1987

Civin C I, "Human Stem Cells and Monoclonal Antibodies", U.S. Pat. No. 4,965,204, issued Oct. 23, 1990

Civin C I, "Human Stem Cells and Monoclonal Antibodies", U.S. Pat. No. 5,035,994, issued Jul. 30, 1991

Civin C I, "Human Stem Cells and Monoclonal Antibodies", U.S. Pat. No. 5,130,144, issued Jul. 14, 1992

Clarke et al, "Prospective Identification and Characterization of Breast Cancer Stem Cells", international publication WO 03/050502, published Jun. 19, 2003

Collins et al, "Identification and isolation of human prostate epithelial stem cells based on alpha(Z)beta(1)-integrin expression", *J Cell Sci* 114:3865-3872 (2001)

Colombel et al, "Zonal variation of apoptosis and proliferation in the normal prostate and in benign prostatic hyperplasia", *Br J Urol* 82:380-385 (1998)

Cress et al, "The alpha 6 beta 1 and alpha 6 beta 4 integrins in human prostate cancer progression", *Cancer Metastasis Rev* 14:219-228 (1995)

Cunha et al, "The endocrinology and developmental biology of the prostate", *Endocr Rev* 8:338-362 (1987a)

Cunha et al, "Mesenchymal-epithelial interactions: technical considerations", *Prog Clin Biol Res* 239:273-282 (1987b)

Davison et al, "Bisamide Bisthiol Compounds Useful for Making Technetium Radiodiagnostic Renal Agents", U.S. Pat. No. 4,673,562, issued Jun. 16, 1987 de Haan et al, "In vitro generation of long-term repopulating hematopoietic stem cells by fibroblast growth factor-1", *Dev Cell* 4(2):241-251 (2003)

De Marzo et al, "Proliferative inflammatory atrophy of the prostate: implications for prostatic carcinogenesis", *Am J Patho* 155:1985-1992 (1999)

De Marzo et al, "Stem cell features of benign and malignant prostate epithelial cells", *J Urol* 160(6 Pt 2):2381-2392 (1998)

Domen et al, "Hematopoietic stem cells and other hematopoietic cells show broad resistance to chemotherapeutic agents in vivo when overexpressing bcl-2", *Exp Hematol* 31:631-639 (2003)

Domen et al, "The role of apoptosis in the regulation of hematopoietic stem cells: Overexpression of Bcl-2 increases both their number and repopulation potential", *J Exp Med* 191:253-264 (2000a)

Domen et al, "Hematopoietic stem cells need two signals to prevent apoptosis; BCL-2 can provide one of these, Kitl/c-Kit signaling the other", *J Exp Med* 192:1707-1718 (2000b)

Donjacour et al, "Assessment of prostatic protein secretion in tissue recombinants made of urogenital sinus mesenchyme and urothelium from normal or androgen-insensitive mice", *Endocrinology* 132(6):2342-2350 (1993)

Douglas et al, "Targeted gene delivery by tropism-modified adenoviral vectors", *Nature Biotechnology* 14(11):1574-1578 (1996)

Falciatori et al, "Identification and enrichment of spermatogonial stem cells displaying side-population phenotype in immature mouse testis", *FASEB J* 183376-183378 (2004)

Fingl et al, in *The Pharmacological Basis of Therapeutics*, 5$^{th}$ Ed., Chapter 1, p 1, McGraw-Hill Companies, (1975)

Fortunel et al, "Comment on 'Stemness': transcriptional profiling of embryonic and adult stem cells" and "A stem cell molecular signature'", *Science* 302:393; author reply 393 (2003)

Fuchs et al, "Socializing with the neighbors: stem cells and their niche", *Cell* 116:769-778 (2004)

Galinsky et al (Eds.), *Remington's Pharmaceutical Sciences*, 20$^{th}$ Ed. (Mack Publishing Co., Easton, Pa.) (2000)

Goodell M A, "Multipotential stem cells and 'side population' cells", *Cytotherapy* 4:507-508 (2002)

Goodell et al, "Dye efflux studies suggest that hematopoietic stem cells expressing low or undetectable levels of CD34 antigen exist in multiple species", *Nat Med* 3:1337-1345 (1997)

Goodell et al, "Isolation and functional properties of murine hematopoietic stem cells that are replicating in vivo", *J Exp Med* 183:1797-1806 (1996)

Gu et al, "Laminin isoform-specific promotion of adhesion and migration of human bone marrow progenitor cells", *Blood* 101:877-885 (2003)

Gussoni et al, "Dystrophin expression in the mdx mouse restored by stem cell transplantation", *Nature* 401:390-394 (1999)

Harlow et al, *Antibodies. A Laboratory Manual*, Cold Spring Harbor Laboratory (1988)

Hierlihy et al, "The post-natal heart contains a myocardial stem cell population", *FEBS Lett* 530:239-243 (2002)

Hockenbery et al, "BCL2 protein is topographically restricted in tissues characterized by apoptotic cell death", *Proc Natl Acad Sci USA* 88:6961-6965 (1991)

Isaacs J T "Control of cell proliferation and cell death in the normal and neoplastic prostate: A stem cell model" in *Benign Prostatic Hyperplasia*, Vol. II (Rodgers et al Eds.), NIH Publication No. 87-2881, Washington D.C.: Department of Health and Human Services, pp. 85-94 (1987)

Ito et al, "Hematopoietic stem cell and progenitor defects in Sca-1/Ly-6A-null mice", *Blood* 101:517-523 (2003)

Jones et al, "Separation of human epidermal stem cells from transit amplifying cells on the basis of differences in integrin function and expression", *Cell* 73:713-724 (1993)

Jones et al, "Sensenbrenner. Two phases of engraftment established by serial bone marrow transplantation in mice", *Blood* 73(2):397-401 (1989)

Kato et al, "Conjugate Having Cytotoxicity and Process for the Preparation thereof", U.S. Pat. No. 4,507,234, issued Mar. 26, 1985

Karhadkar et al, "Hedgehog signalling in prostate regeneration, neoplasia and metastasis", *Nature* 431:707-12 (2004)

Kaur et al, "Adhesive properties of human basal epidermal cells: an analysis of keratinocyte stem cells, transit amplifying cells, and postmitotic differentiating cells", *J Invest Dermatol* 114:413-420 (2000)

Kinbara et al, "Evidence of stem cells in the adult prostatic epithelium based upon responsiveness to mesenchymal inductors", *Prostate* 29(2):107-116 (1996b)

Kohler et al, "Derivation of specific antibody-producing tissue culture and tumor lines by cell fusion", *Eur J Immunol* 6:511-519 (1976)

Kohn et al, "Non-Peptide Polyamino Acid Bioerodable Polymers", U.S. Pat. No. 4,638,045, issued Jan. 20, 1987

Kyprianou et al, "Expression of transforming growth factor-beta in the rat ventral prostate during castration-induced programmed cell death", *Mol Endocrinol* 3:1515-1522 (1989)

Lapidot et al, "A cell initiating human acute myeloid leukaemia after transplantation into SCID mice", *Nature* 367:645-648 (1994)

Lavker et al, "Epidermal stem cells: properties, markers, and location", *Proc Natl Acad Sci USA* 97(25):13473-13475 (2000)

Lee et al, "Prostatic ductal system in rats: regional variation in morphological and functional activities", *Biol Reprod* 43(6):1079-1086 (1990)

Lemischka et al, "Stem cells: interactive niches", *Nature* 425(6960):778-779 (2003)

Li et al, "Identification and isolation of candidate human keratinocyte stem cells based on cell surface phenotype", *Proc Natl Acad Sci USA* 95:3902-3907 (1998)

Loken et al, "Method to Determine Composition of Bone Marrow Samples", U.S. Pat. No. 5,137,809, issued Aug. 11, 1992

Maggio-Price et al, "Evaluation of stem cell reserve using serial bone marrow transplantation and competitive repopulation in a murine model of chronic hemolytic anemia", *Exp Hematol* 16(8):653-659 (1988)

Martin et al, "Thiol Reactive Liposomes", U.S. Pat. No. 4,429,008, issued Jan. 31, 1984

Matsuura et al, "Adult cardiac Sca-1-positive cells differentiate into beating cardiomyocytes", *J Biol Chem* 279:11384-11391 (2004)

Mayhew et al, "Liposome Drug Delivery Method and Composition", U.S. Pat. No. 4,873,088, issued Oct. 10, 1989

McDonnell et al, "Expression of the protooncogene bcl-2 in the prostate and its association with emergence of androgen-independent prostate cancer", *Cancer Res* 52:6940-6944 (1992)

Michael et al, "Binding-incompetent Adenovirus Facilitates Molecular Conjugate-mediated Gene Transfer by the Receptor-mediated Endocytosis Pathway", *J Biol Chem* 268(10):6866-6869 (1993)

Montanaro et al, "Skeletal muscle enqraftment potential of adult mouse skin side population cells", *Proc Natl Acad Sci USA* 100:9336-9341 (2003)

Morrison et al, "Transient Notch activation initiates an irreversible switch from neurogenesis to gliogenesis by neural crest stem cells", *Cell* 101(5):499-510 (2000)

Murayama et al, "Flow cytometric analysis of neural stem cells in the developing and adult mouse brain", *J Neurosci Res* 69:837-847 (2002)

Nemeth et al, "Prostatic ductal system in rats: regional variation in stromal organization", *Prostate* 28(2):124-128 (1996)

Norman et al, "The induction of new ductal growth in adult prostatic epithelium in response to an embryonic prostatic inductor", *Prostate* 8(3):209-220 (1986)

Pardal et al, "Applying the principles of stem-cell biology to cancer", *Nat Rev Cancer* 3:895-902 (2003)

Passegue et al, "Normal and leukemic hematopoiesis: are leukemias a stem cell disorder or a reacquisition of stem cell characteristics?", *Proc Natl Acad Sci USA* 1:11842-11849 (2003)

Paul, *Fundamental Immunology*, 3rd ed., Raven Press, pp. 243-247 (1993)

Potten et al, "Regulation and significance of apoptosis in the stem cells of the gastrointestinal epithelium", *Stem Cells* 15:82-93 (1997)

Reya et al, "Wnt signalling in stem cells and cancer", *Nature* 434(7035):843-850 (2005)

Reya et al, "A role for Wnt signalling in self-renewal of haematopoietic stem cells", *Nature* 423(6938):409-414 (2003)

Reya et al, "Stem cells, cancer, and cancer stem cells", *Nature* 414 (6859):105-111 (2001)

Richardson et al, "CD133, a novel marker for human prostatic epithelial stem cells", *J Cell Sci* 117:3539-3545 (2004)

Rodwell et al, "Antibody Conjugates for the Delivery of Compounds to Target Sites", U.S. Pat. No. 4,671,958, issued June 9, Rouleau et al, "Ductal heterogeneity of cytokeratins, gene expression, and cell death in the rat ventral prostate", *Mol Endocrinol* 4(12):2003-2013 (1990)

Rust et al, "The Promise of Integrins as Effective Targets for Anticancer Agents", *J Biomed Biotechnol* 2:124-130 (2002)

Salm et al, "Differentiation and stromal-induced growth promotion of murine prostatic tumors", *Prostate* 51(3):175-188 (2002)

Scharenberg et al, "The ABCG2 transporter is an efficient Hoechst 33342 efflux pump and is preferentially expressed by immature human hematopoietic progenitors", *Blood* 99:507-512 (2002)

Schoonjans et al, "Multipurpose Antibody Derivatives", U.S. Pat. No. 6,809,185, issued Oct. 26, 2004

Senter et al, "Cell-Delivery Agent", U.S. Pat. No. 4,625,014, issued Nov. 25, 1986

Shapiro et al, "The relative proportion of stromal and epithelial hyperplasia is related to the development of symptomatic benign prostate hyperplasia", J Urol 147(5):1293-1297 (1992)

Shih et al, "Tumoricidal Methotrexate-Antibody Conjugate, U.S. Pat. No. 4,699,784, issued Oct. 13, 1987

Shinohara et al, "beta- and alpha6-integrin are surface markers on mouse spermatogonial stem cells", Proc Natl Acad Sci USA 96(10):5504-5509 (1999)

Shou et al, "Dynamics of Notch Expression during Murine Prostate Development and Tumorigenesis", Cancer Res 61(19): 7291-7297 (2001)

Slack-Davis et al, "Emerging views of integrin signaling implications for prostate cancer", J Cell Biochem 91:41-46 (2004)

Spangrude et al, "Purification and characterization of mouse hematopoietic stem cells", Science 241:58-62 (1988)

Spitler L E, "Composition and Method of Transplantation Therapy", U.S. Pat. No. 4,489,710

Spradling et al, "Stem cells find their niche", Nature 414 (6859):98-104 (2001)

Srivastava P C, "Radioiodinated maleimides and use as agents for radiolabeling antibodies", U.S. Pat. No. 4,735, 792, issued Apr. 5, 1988

Sugimura et al, "Morphogenesis of ductal networks in the mouse prostate", Biol Reprod 34(5):961-971 (1986a)

Sugimura et al, "Morphological and histological study of castration-induced degeneration and androgen-induced regeneration in the mouse prostate", Biol Reprod 34(5): 973-983 (1986b)

Suzuki et al, "Flow-cytometric separation and enrichment of hepatic progenitor cells in the developing mouse liver", Hepatology 32(6):1230-1239 (2000)

Takao et al, "Stromal/epithelial interactions of murine prostatic cell lines in vivo: a model for benign prostatic hyperplasia and the effect of doxazosin on tissue size", Prostate 54(1):17-24 (2003)

Tani et al, "Enrichment for murine keratinocyte stem cells based. on cell surface phenotype", Proc Natl Acad Sci USA 97(20):10960-10965 (2000)

Tiberio et al, "Keratinocytes enriched for stem cells are protected from anoikis via an integrin signaling pathway in a Bcl-2 dependent manner", FEBS Lett 524:139-144 (2002)

Tsujimura et al, "Proximal location of mouse prostate epithelial stem cells: a model of prostatic homeostasis", J Cell Biol 157(7):1257-1265 (2002)

Tsukamota et al, "Human Hematopoietic Stem Cell", U.S. Pat. No. 5,750,397, issued May 12, 1998

Uchida et al, "Transplantable hematopoietic stem cells in human fetal liver have a CD34(+) side population (SP) phenotype", J Clin Invest 108:1071-1077 (2001)

Valk-Lingbeek et al, "Stem cells and cancer; the polycomb connection", Cell 118:409-418 (2004)

Varambally et al, "The polycomb group protein EZH2 is involved in progression of prostate cancer", Nature 419: 624-629

Walsh et al, "Expression of Wnt and Notch pathway genes in a pluripotent human embryonal carcinoma line and embryonic stem cell", APMIS 111(1):197-201; discussion 210-201 (2003)

Walsh P (Ed), Physicians' Desk Reference, 55th Edition, (Montvale, N.J.: Medical Economics Company (2001)

Watt F M, "Role of integrins in regulating epidermal adhesion, growth and differentiation", EMBO J 21:3919-3926 (2002)

Welm et al, "Sca-1(pos) cells in the mouse mammary gland represent an enriched progenitor cell population", Dev Biol 245 (1):42-56 (2002)

Willert et al, "Wnt proteins are lipid-modified and can act as stem cell growth factors", Nature 423(6938):448-452 (2003)

Xin et al, "In vivo regeneration of murine prostate from dissociated cell populations of postnatal epithelia and urogenital sinus mesenchyme", Proc Natl Acad Sci USA 100 (Suppl 1):11896-11903 (2003)

Yin et al, "AC133, a novel marker for human hematopoietic stem and progenitor cells", Blood 90(12):5002-5012 (1997)

Zhou et al, "The ABC transporter Bcrpl/ABCG2 is expressed in a wide variety of stem cells and is a molecular determinant of the side-population phenotype", Nat Med 7:1028-1034 (2001)

Zhou et al, "Bcrpl gene expression is required for normal numbers of side population stem cells in mice, and confers relative protection to mitoxantrone in hematopoietic cells in vivo", Proc Natl Acad Sci USA 99:12339-12344 (2002)

Accession No. M14745: Human Bcl-2 mRNA; LOCUS: HUMBCL2C

What is claimed is:

1. An isolated population of prostatic stem cells expressing alpha 6 integrin and at least one substance selected from the group consisting of Bcl-2, FGFR, prominin, CD34, a Notch protein, and a Frizzled protein, wherein the prostatic stem cells are obtained from the proximal region of ducts of the prostate, and more than 60% of said prostatic stem cells co-express alpha 6 integrin and Bcl-2.

2. The population of claim 1, wherein said prostatic stem cells are prostatic tumor stem cells.

3. The population of claim 1, wherein the prostatic stem cells consist of cells that co-express alpha 6 integrin and Bcl-2 and at least one substance selected from the group consisting of FGFR, prominin, CD34, a Notch protein, and a Frizzled protein.

4. The population of claim 3, wherein the prostatic stem cells express alpha 6 integrin, Bcl-2, FGFR, prominin, CD34, a Notch protein, and a Frizzled protein.

* * * * *